(12) United States Patent
Chung et al.

(10) Patent No.: US 9,862,955 B2
(45) Date of Patent: Jan. 9, 2018

(54) **PLANT ENDOPHYTIC BACTERIA *BACILLUS ORYZICOLA* ISOLATED FROM RICE RIZHOSPHERE, AND DEVELOPMENT OF AGENT FOR NATURAL PLANT PROTECTION AND PLANT ENHANCEMENT USING THE SAME**

(71) Applicant: JGREEN INDUSTRY INC., Gyeongsangnam-do (KR)

(72) Inventors: Young Ryun Chung, Gyeongsangnam-do (KR); Mohammad Tofajjal Hossain, Hathazari (BD); Eu Jin Chung, Gyeongsangnam-do (KR); Geun Gon Kim, Gyeongsangnam-do (KR); Jung Eun Lee, Gyeongsangnam-do (KR)

(73) Assignee: JGREEN INDUSTRY INC., Gyeongsangnam-Do (KR)

( * ) Notice: Subject to any disclaimer, the term of this patent is extended or adjusted under 35 U.S.C. 154(b) by 0 days.

(21) Appl. No.: 15/314,267

(22) PCT Filed: May 28, 2015

(86) PCT No.: PCT/KR2015/005342
§ 371 (c)(1),
(2) Date: Nov. 28, 2016

(87) PCT Pub. No.: WO2015/183003
PCT Pub. Date: Dec. 3, 2015

(65) Prior Publication Data
US 2017/0191072 A1    Jul. 6, 2017

(30) Foreign Application Priority Data
May 28, 2014   (KR) .................. 10-2014-0064712

(51) Int. Cl.
*C12N 1/21*      (2006.01)
*C12N 15/75*     (2006.01)
*C12N 1/20*      (2006.01)
*C05F 11/00*     (2006.01)

(52) U.S. Cl.
CPC .............. *C12N 15/75* (2013.01); *C05F 11/00* (2013.01); *C12N 1/20* (2013.01)

(58) Field of Classification Search
None
See application file for complete search history.

(56) References Cited

FOREIGN PATENT DOCUMENTS

| KR | 10-2007-0038855 A | 4/2007 |
| KR | 10-2010-0116562 A | 11/2010 |
| KR | 10-2012-0051284 A | 5/2012 |
| KR | 10-2013-0005592 A | 1/2013 |

OTHER PUBLICATIONS

Madhaiyan, M. et al., *Bacillus methylotrophicus* sp. nov., a methanol-utilizing, plant-growth-promoting bacterium isolated from rice rhizosphere soil. Int J Syst Evol Microbiol 60:2490-2495.(2010).
Chert, C. et al., Biological control of Fusarium whilt of cotton by use of endophytic bacteria. Biol Cont 5:10-16, 1995.
Rosenblueth, M. et al., Bacterial endophytes and their interactions with hosts. Molecular Plant-Microbe Interactions 19: 827-837, 2006.
de Matos Nogueira, E. et al., Expression of sugarcane genes induced by inoculation with Gluconacetobacter diazotrophicus and Herbaspirillum rubrisubalbicans. Genet. Mol. Biol. 24: 199-206, 2001.
Bibi, F et al., Diversity and characterization of endophytic bacteria associated with tidal flat plants and their antagonistic effects on oomycetous plant pathogens. Plant Pathol J 28:20-31, 2012.
Cao, C. et al., Biopesticide controls of plant diseases: resources and products for organic farmers in Ohio. Fact Sheet, Agricultural and Natural Resources. SAG-18-10 The Ohio State University, 2010.
Kim, B. K. et al., Genome sequence of the leaf-colonizing bacterium *Bacillus* sp. strain 5B6, isolated from a cherry tree. J Bacteriol 194:3758-3759, 2012.
Yan, X. et al., Antagonistic bioactivity of endophytic strains isolated from Salvia mitiorrhiza. Afr J Biotech 10:15117-15122, 2011.
Aslam, Z. et al., Diversity of the bacterial community in the rice rhizosphere managed under conventional and no-tillage practices. J Microbiol 51:747-756, 2013.
Gatson, J. W. et al., *Bacillus tequilensis* sp. nov., isolated from a 2000-year-old Mexican shaft-tomb, is closely related to Bacillus subtilis. Int J Syst Evol Microbiol 56:1475-1484, 2006.
Sumpavapol, P. et al. *Bacillus siamensia* sp. nov., isolated from salted crab (poo-khem) in Thailand. Int J Syst Evol Microbial 60:2364-2370, 2010.

*Primary Examiner* — Jim Ketter
(74) *Attorney, Agent, or Firm* — The PL Law Group, PLLC

(57) ABSTRACT

A strain has a microorganism fertilizer efficacy and can be used as a biopesticide, by isolating multi-functional plant endophytic bacteria, which can widely suppress the growth of plant-pathogenic fungi and bacteria and specifically act on rice as a host plant, thereby retaining both a disease resistance inducing effect and a plant growth promoting effect, followed by mass-culturing and formulating. The present invention provides novel microorganism *Bacillus oryzicola* or *Bacillus oryzicola* having a DNA-DNA relatedness value of 70% or more with the *Bacillus oryzicola*.

7 Claims, 12 Drawing Sheets

FIG.5

SEQUENCE LISTING

```
<160> NUMBER OF SEQ ID NOS: 2

<210> SEQ ID NO 1
<211> LENGTH: 1513
<212> TYPE: DNA
<213> ORGANISM: Bacillus oryzicola

<400> SEQUENCE: 1
cgagtttgat catggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aatactggat ggttgtttga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttaggaagaa caagtgccg ttcaaatagg gcggcacctt      480
gacggtacct aaccagaaag ccacggctaa ctacgtgcca gcagccgcgg taatacgtag     540
gtggcaagcg ttgtccggaa ttattgggcg taaagggctc gcaggcggtt tcttaagtct     600
gatgtgaaag ccccggctc aaccggggag ggtcattgga aactggggaa cttgagtgca      660
gaagaggaga gtggaattcc acgtgtagcg gtgaaatgcg tagagatgtg gaggaacacc     720
agtggcgaag gcgactctct ggtctgtaac tgacgctgag gagcgaaagc gtgggagcg      780 aacaggatta gataccctgg tagtccacgc cgtaaacgat gagtgctaag tgttaggggg     840
tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagatatag    1020
gacgtcccct tcgggggcag agtgacaggt ggtgcatggt tgtcgtcagc tcgtgtcgtg    1080
agatgttggg ttaagtcccg caacgagcgc aacccttgat cttagttgcc agcattcagt    1140
tgggcactct aaggtgactg ccggtgacaa accggaggaa ggtggggatg acgtcaaatc    1200
atcatgcccc ttatgacctg gctacacac gtgctacaat ggacagaaca aagggcagcg     1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
```

-continued

```
gaggtaacct tttaggagcc agccgccgaa ggtgggacag atgattgggg tgaagtcgta    1500
acacgtaacc gta                                                        1513

<210> SEQ ID NO 2
<211> LENGTH: 1513
<212> TYPE: DNA
<213> ORGANISM: Bacillus oryzicola

<400> SEQUENCE: 2
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aatactggat ggttgtttga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga caagtgccg ttcaaatagg gcggcacctt     480
gacggtacct aaccagaaag ccacggctaa ctacgtgcca gcagccgcgg taatacgtag     540
gtggcaagcg ttgtccggaa ttattgggcg taaagggctc gcaggcggtt tcttaagtct     600
gatgtgaaag cccccggctc aaccggggag ggtcattgga aactgggaa cttgagtgca     660 gaagaggaga gtggaattcc acgtgtagcg gtgaaatgcg tagagatgtg gaggaacacc     720
agtggcgaag gcgactctct ggtctgtaac tgacgctgag gagcgaaagc gtgggagcg     780 aacaggatta gataccctgg tagtccacgc cgtaaacgat gagtgctaag tgttaggggg     840
tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagagatag    1020 gacgtccct tcggggcag agtgacaggt ggtgcatggt tgtcgtcagc tcgtgtcgtg     1080
agatgttggg ttaagtcccg caacgagcgc aacccttgat cttagttgcc agcattcagt    1140
tgggcactct aaggtgactg ccggtgacaa accggaggaa ggtggggatg acgtcaaatc    1200
atcatgcccc ttatgacctg gctacacac gtgctacaat ggacagaaca aagggcagcg    1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct tttaggagcc agccgccgaa ggtgggacag atgattgggg tgaagtcgta    1500
acaaggtgcc gta                                                       1513
```

PLANT ENDOPHYTIC BACTERIA *BACILLUS ORYZICOLA* ISOLATED FROM RICE RIZHOSPHERE, AND DEVELOPMENT OF AGENT FOR NATURAL PLANT PROTECTION AND PLANT ENHANCEMENT USING THE SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/005342, filed May 28, 2015, which claims priority to the benefit of Korean Patent Application No. 10-2014-0064712 filed in the Korean Intellectual Property Office on May 28, 2014, the entire contents of which are incorporated herein by reference.

BACKGROUND

1. Technical Field

The present invention relates to a plant endophytic microorganism and a microorganism formulation containing the same, and more particularly, to a novel microorganism *Bacillus oryzicola* and a microorganism formulation containing the same.

The present invention has been deduced from studies executed as a part of: the 'Next-Generation Biopesticide Development Project' (Project File No. 10044909, Project Title: Development of next-generation microorganism material for plant disease control using antagonist microorganisms) supported by the Ministry for Food, Agriculture, Forestry and Fisheries in 2010 and the 'Industrial Convergence Core Technology Development Project' supported by the Ministry of Industry and Trade in 2013 (Project File No. 808015-3-2, Project Title: Development of broad spectrum probiotic crop protective agent having sustained effects (2010-2013).

2. Background Art

Over the last few decades around the world, in order to increase a quantity of agricultural crops such as grains, greens, fruits, etc., a great amount of chemical fertilizer and agricultural pesticides for control of disease and insect pests, and weed control, have been used. Due to such a continuous use of chemical fertilizer and agricultural pesticides, some problems such as soil acidification, loss of soil fertility, environmental contamination, ecocide, mammal toxicity, causing pesticide resistance of disease and insect pests and weeds, or the like, have been consistently raised. Further, due to an abnormal climate change caused by an increase in amount of atmospheric carbon dioxide, continuous drought and salt accumulation in agricultural lands are now endangering stable production of agricultural crops.

In order to overcome the above-described problems, efforts for reducing amounts of used chemical fertilizer and agricultural pesticides have been made at home and abroad, and in particular, since the Act on the Support of Environmentally-friendly Agriculture was originally established in 1999, Korean policy has been carried now forward a third environmentally-friendly agriculture promotion. The goal of this plan is to accomplish a reduction in amounts of used chemical fertilizer and agricultural pesticides by about 15% till 2015, compared to 2011. At the same time, as a national requirement for safe foodstuffs is increasing due to an elevated living level in a social aspect, and eco-friendly agricultures such as an organic agriculture or natural agriculture oriented to the preservation of environment for agricultural production and natural ecosystem are rapidly expanding, such that studies on development of novel fertilizer and biological pesticides using microorganisms able to replace existing chemical fertilizer and pesticides are also rapidly increased. Multinational companies having well known the limitations in using the chemical fertilizer and pesticides, have recently developed and distributed biological agents, that is, plant activity enhancing agents able to compensate the above limitations. On the other hand, the multinational companies have conducted a seed development of drought-resistant crops possible to grow and develop even in some regions with serious drought or salt accumulation. Such developed microorganism products are formulated by selecting microorganisms having specific functions from the natural environment, and mass-culturing the same. The formulated microorganism products may be used for foliar spray or as a granular agent for soil treatment to prevent disease and insect pests, or otherwise, may also be used as the microorganism fertilizer or plant enhancing agent (see Non-Patent Document 1).

The microorganisms used herein are widely distributed in the natural environment such as soil, plant rhizosphere, ocean, etc., and have diversity in species and secrete different types of metabolites, thereby being effectively used in the environmentally-ecofriendly agriculture. Using the microorganisms may be generally classified into three types, including: directly using the microorganism itself; using metabolites produced by microbiologic fermentation; and using microorganism metabolites as a leading compound for novel synthesis of pesticides, or the like. Among these, the most used method is to directly use antagonistic microorganisms able to inhibit plant pathogens, plant growth promoting rhizobacteria (PGPR) and endophytic microorganisms to promote plant growth. In particular, studies on plant disease-resistance by these microorganisms have been greatly conducted.

Among diverse microorganisms, studies on endophytic bacteria have been actively made at the home and abroad in recent 10 years. Herein, the endophytic bacteria are defined as bacteria present in a tissue of a healthy and living plant to provide various advantages without any substantial harm to the plant. In general, it is known that the endophytic bacteria may be present in a space between plant cells or inside the cells, directly or indirectly induce resistance to disease, insect pests and stress, and have a great influence upon the growth of the plant. More particularly, it is presumed that the endophytic bacteria induce nitrogen fixation, solubilization of phosphoric acid, siderophore production, generation of active hormone, production of an antibacterial material or disease resistance of the plant, thereby preventing pathogenic infection and promoting plant growth (see Non-Patent Documents 1 to 4). Such endophytic bacteria are affinitive to a host plant and may form a symbiotic relationship in the tissue of the host plant without being recognized as the pathogenic bacteria, (see Non-Patent Document 5). Some specific endophytic bacteria may provide plant growth promoting effect and disease control effect by simultaneously using one or more mechanisms. Otherwise, different mechanisms may be applied during different periods in the life of plant. A plant gene may be changed by the presence of bacteria, and such changed gene may occasionally leave a clue to effects of the endophytic bacteria in the plant (see Non-Patent Document 6). The endophytic bacteria are proliferated inside the cells, wherein an entire density of the bacteria is high in a root and a beginning part of a stem, and is gradually reduced toward higher parts of the plant such as stems, leaves, etc. In a case of a corn leaf, it has been found that the density of the bacteria ranged from about $1 \times 10^3$ to $1 \times 10^7$ cfu/g. As the endophytic bacteria isolated up to now, about 130 species in about 50 genera including, for example, *Bacillus, Pseudomonas, Enterobacter, Agrobacterium*, or the like, have been discovered. These bacteria could assist the growth of economically important crops such as tomato, potato, corn and rice while suppressing an attack of diseases, thereby increasing the production of crops.

The rice is one of the top five crops in the world but involves production loss due to diverse diseases. Among these, a damage caused by pathogenic fungi such as rice blast, rice sheath blight, etc. incurred a fatal loss in crop production, and therefore, has been effectively prevented by developing resistant cultivars and developing chemical pesticides up to now. However, a bakanae, grain rot and bacterial blight, etc. of bacterial diseases, which are caused by seed transmission bacterial diseases, other than the above diseases also occur very often in some regions and cause a great damage. In recent years, these diseases have been difficult in their control. These pathogens overwinter in a rice paddy or the tissue of surrounding weeds, and in particular, since the rice is vulnerable to the pathogens under warm and moist conditions, it is difficult to control the disease if the disease starts to develop once. The control of the pathogens generally depends on chemical pesticides, however, using most of such chemical pesticides has incurred problems such as environmental contamination or mammal toxicity. Therefore, there is a growing interest in eco-friendly biological pesticides capable of replacing the above chemical pesticides.

Several tens species of biological pesticides for prevention of plant disease have been currently developed and commercially available in the internal and external markets. Among these, some effective biological pesticides are mostly manufactured using bacteria *Bacillus* and fungi such as *Trichoderma* (see Non-Patent Documents 7 to 10). *Bacillus* type products may include *B. subtilis, B. pumilus* and *B. amyloliquefaciens*, and most of these strains are known to have a mechanism of secreting an antibiotic material, that is, cyclic peptide such as iturin, surfactin, etc., to directly inhibit the pathogen, otherwise, to induce disease-resistance of the host. *Bacillus* sp. forms endospores and is survived for a long period of time even under poor natural environments, and because of quite high antibacterial ability, many researchers have investigated and published results thereof in regard to biological control of plant diseases (see Non-Patent Document 10). Other than those mentioned above, some results of studying novel endophytic bacteria, that is, *Bacillus methylotropicus* have recently reported. This strain was firstly isolated and defined with a nomenclature in Korea in 2010, and has been identified to have plant growth promoting ability (see Non-Patent Document 1). Following this, the above bacteria was isolated from ginseng, tomato and potato rhizospheres and reported to have pathogen inhibitory ability and plant growth promoting effect in China (see Non-Patent Documents 11 to 13). However, these studies do not include results in regard to induction of disease-resistance of the host plant or inhibition of other diseases, other than the antibacterial ability of the above strain to the plant pathogens. Studies on the endophytic microorganisms of rice have been mostly made by researchers in cultivation areas of rice, that is, Korea, China, etc., and researches into the comparison of a rhizospheric bacteria colony with latest practical and no-till paddy rice in each growth time period have been published. According to such research results, it was reported that the bacteria colony belonging to Proteobacteria were more found in the no-till paddy rice, while diverse bacteria belonging to Firmicutes, in particular, *Bacillus* sp. have been discovered in a relatively high ratio in a rice rhizosphere according to the practical agriculture (see Non-Patent Document 14). Further, it was reported that various species of *Bacillus* sp., *Paenibacillus* sp. and *Pseudomonas* sp., which inhibit the growth of pathogens such as rice blast or bakanae, have been isolated from the rice rhizospheres (see Non-Patent Document 15). Although such studies on diversity of different bacteria species living in the rice rhizosphere have been partially conducted, a research into novel bacteria having different functions while specifically acting on the rice as proposed in the present invention is still not disclosed. Besides, much researches have been done on the types of *Bacillus* sp. isolated from specific environments, however, only a few species thereof have been commercialized and are now effectively used for the plant control (see Non-Patent Documents 16 and 17). One reason of this fact is presumed that the pest control effect may be relatively low because a mechanism for inhibiting pathogens only was adopted as a standard when isolating the antagonist bacteria. Accordingly, in order to more effectively prevent a disease while expressing characteristics of the above strain, it is necessary to investigate and develop novel multi-functional microorganisms able to simultaneously endow an ability of inducing disease-resistance of the host plant and effects of promoting a growth of the host plant, thereby enhancing the host plant.

SUMMARY

Accordingly, in order to compensate the above drawbacks, an object of the present invention is to develop and provide a novel microorganism formulation having all of microorganism fertilizer efficacy, plant-enhancing efficacy and plant protection efficacy by isolating novel multi-functional plant endophytic bacteria, which can widely suppress a growth of plant-pathogenic fungi and bacteria and specifically act on rice as a host plant, thereby retaining both of disease resistance inducing effect and plant growth promoting effect, followed by mass-culturing and formulating the same.

In order to achieve the above-described object, according to an aspect of the present invention, there is provided a novel microorganism *Bacillus oryzicola* or *Bacillus oryzicola* having a DNA-DNA relatedness value of 70% or more relative to the above *Bacillus oryzicola*.

Herein, the *Bacillus oryzicola* may include 16S rRNA having a base sequence represented by SEQ ID NO: 1 or SEQ ID NO: 2.

In addition, the *Bacillus oryzicola* may be *Bacillus oryzicola* YC7007 (Deposit No: KCCM11275P) or *Bacillus oryzicola* YC7010 (Deposit No: KACC18228).

Further, the *Bacillus oryzicola* may have plant disease resistance inducing efficacy.

Further, the plant disease may be at least one selected from a group consisting of grain rot, bacterial blight, panicle blight and bakanae disease.

In addition, the *Bacillus oryzicola* may further have plant pathogen inhibitory efficacy, plant growth promoting efficacy and plant enhancing efficacy.

Further, the plant growth promoting efficacy may be plant growth promoting efficacy in relation to rice.

According to another aspect of the present invention, there is provided a microorganism formulation for fertilizer, plant protection and plant enhancement use, including the above microorganism, and a culture solution or culture filtrate thereof as an active ingredient.

According to the present invention, it is possible to provide an excellent microorganism formulation containing multi-functional bacteria, which can simultaneously play roles of a natural plant protector, plant enhancer and microorganism fertilizer, compared to existing bacteria reported in the art, by using multi-functional bacteria *Bacillus oryzicola* which can simultaneously inhibit the growth of significant plant pathogenic fungi and bacteria in the crop and have not only effect of inducing disease-resistance of a host plant but also effect of promoting a growth of the host plant, characterized in that the formulation may secrete an antibiotic material and a material for promoting the growth and for inducing systemic acquired disease-resistance of the host, thus to directly inhibit plant pathogens, and may specifically act on the rice to express a growth promoting ability and a systemic acquired disease resistance inducing ability.

BRIEF DESCRIPTION OF DRAWINGS

FIG. 5 is a photograph illustrating for distinction and comparison of treatment to explain a bacterial blight prevention effect.

DETAILED DESCRIPTION

Figure 1A:
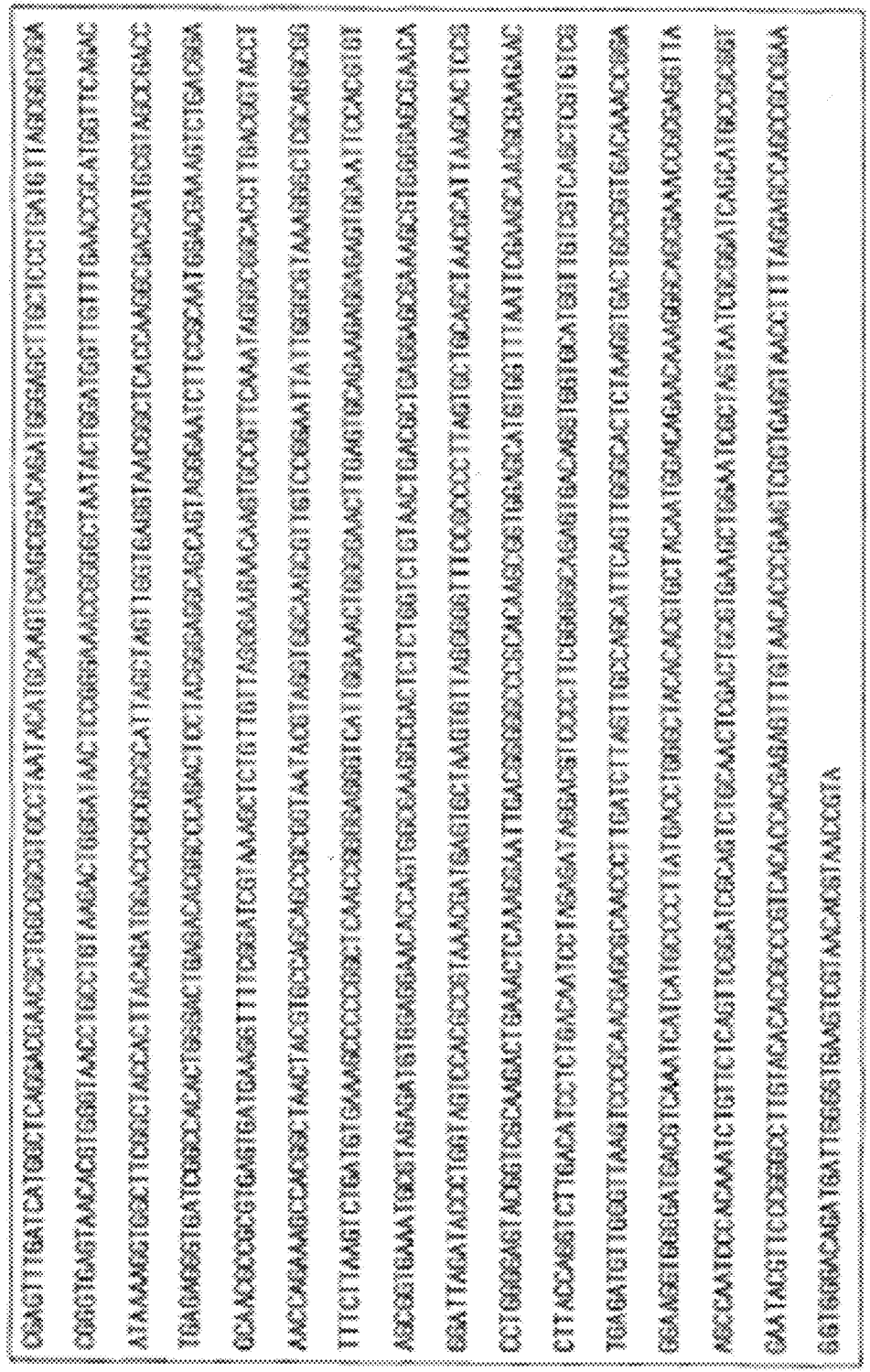
FIGS. 1(*a*) and 1(*b*) are views illustrating base sequences of 16S rRNA genes of YC7007 strain and YC7010 strain, respectively.

Hereinafter, the present invention will be described in detail with reference to examples. Prior to this, terminologies or words used in the detailed description and claims of the present description are not limited to common or dictionary meanings thereof. Instead, on the basis of the principle that an inventor may suitably define the concept of a term in order to explain the invention of himself or herself by the best way, these must be construed of having the meanings and concepts according to the technical spirit of the present invention. Accordingly, the configuration of examples stated in the present description is a preferred embodiment of the present invention only, and does not represent all the technical spirit of the present invention. Therefore, it would be appreciated that diverse equivalents and modifications replaceable at the time of filing the present application could be present.

The present inventors have discovered a new strain that can be used as a novel form of biopesticide having microorganism fertilizer efficacy by isolating multi-functional endophytic bacteria, which can widely inhibit the growth of plant pathogenic fungi and bacteria while specifically acting on the rice as a host plant, thus to express both of disease-resistance inducing and plant growth promoting effects, followed by mass-culturing and formulating the same.

In other words, as a result of investigating the bacteria isolated from a rice paddy, it was found that novel species of bacteria possess all of the above efficacies. Further, as a result of executing the determination and analysis of base sequence of 16S rRNA gene, DNA-DNA homology experiment, or the like, it was identified as a novel microorganism belonging to *Bacillus* sp. genus, therefore, named "*Bacillus oryzicola* YC7007".

Such a novel microorganism as described in the present invention not only includes *Bacillus oryzicola*, but also should be construed that, if there is DNA-DNA hybridization on the basis of the article of Goris et al. (Goris, J., Konstantinidis, K. T., Klappenbach, J. A., Coenye, T., Vandamme, P., and Tiedje, J M. (2007). DNA-DNA hybridization values and their relationship to whole-genome sequence similarities. Int J Syst Evol Microbiol 57:81-91), some microorganisms expressing a DNA-DNA relatedness value of 70% or more could be included in the *Bacillus oryzicola* according to the present invention. In other words, if DNA-DNA hybridization has been made according to the standard proposed in the article of Goris et al., the microorganism expressing the DNA-DNA relatedness value of 70% or more may be managed as the same microorganism as *Bacillus oryzicola* of the present invention.

According to one preferred embodiment of the present invention, *Bacillus oryzicola* may include 16S rRNA having a base sequence defined with SEQ ID NO: 1 or SEQ ID NO: 2, the *Bacillus oryzicola* may be *Bacillus oryzicola* YC7007 (Deposit No: KCCM11275P) or *Bacillus oryzicola* YC7010 (Deposit No: KACC 18228). (SEQ ID NO: 1 denotes 16S rRNA gene sequence of *Bacillus oryzicola* YC7007 strain according to the present invention, and SEQ ID NO: 2 denotes 16S rRNA gene sequence of *Bacillus oryzicola* YC7010 strain according to the present invention.)

Hereinafter, the present invention will be described in more detail with reference to examples. In the present examples, the description would be given by Example 1 focusing on experiments of YC7007 strain and Example 2 focusing on experiment of YC7010 strain, respectively.

Example 1

Isolation and Identification of YC7007 Strain
(1) Isolation of YC7007 Strain
YC7007 strain was isolated from an internal tissue of roots of the rice growing in a paddy soil of a test field in Gyeongsang National University located in Jinju city of South Korea. First, in order to isolate plant endophytic bacteria, the surface of root cut pieces was sterilized by immersing the cut pieces in a 1% sodium hyperchlorite (NaOCl) solution for 10 minutes. After placing these pieces on 1/10 TSA medium (tryptic soy broth 3 g, agar 16 g/1 l of distilled water), the pieces were cultured for 2 to 3 days, followed by checking the sterilization of the surface while observing the growth of bacteria. 1.0 g of root pieces with sterilized surface was taken and put into a high pressure sterilizer, followed by adding 9.0 ml of sterilized and distilled water thereto and grinding the mixture by means of a sterilized bowl and mortar. 0.1 ml of ground material was taken and put into 0.9 ml of sterilized and distilled water, and then, diluted 10 times ($10^{-3}$), followed by additionally diluting the same by 10 times in order ($10^{-4}$ and $10^{-5}$). The diluted solution was divided into three even parts and distributed on ⅒ TSA medium, and then, homogeneously smeared thereon. This incubator was under incubation at 28° C. for 2 to 3 weeks, and the grown single colony was purely isolated and named YC7007 strain.

(2) Identification of YC7007 Strain

In order to identify the isolated YC7007 strain, morphological, physiological and biochemical features were investigated as follows. Subjected to a standard strain (type species) similar to the isolated YC7007 strain, the morphological feature was investigated using a scanning electron microscope, while the physiological and biochemical features were investigated according to a specific analysis method developed by the present inventors and any typical analysis method, respectively (see Non-Patent Document 7).

The isolated YC7007 strain was gram-positive and had mobility, the cells were in a bar form (with 0.6 μm width, 1.8-2.6 μm length), formed an endophytic spore and could not be grown under an anaerobic condition. Investigated results of physiological and biochemical features of this strain compared to similar type species are shown in Table 1 below, and DNA-DNA relatedness values are shown in Table 2 below. The results of all strains used in Table 1 have been obtained through investigation according to the above analysis method.

TABLE 1

| Characteristic | [a]1 | 2 | 3 | 4 | 5 | 6 | 7 |
|---|---|---|---|---|---|---|---|
| Growth at pH 13 | − | + | − | − | − | + | + |
| Growth at 14% NaCl | − | − | − | − | − | − | + |
| Hydrolysis of | | | | | | | |
| Gelatin | + | − | + | + | + | + | + |
| Carboxymethyl cellulose | − | − | − | − | + | − | − |
| API kits | | | | | | | |
| Arbutin | + | w | − | w | + | w | + |
| D-Lactose | + | w | w | w | − | w | − |
| Starch | + | w | − | w | w | − | + |
| Glycogen | + | w | − | w | w | w | + |
| Gentiobiose | + | w | − | − | − | − | + |
| D-Turanose | − | − | w | − | − | − | − |
| Potassium-5-ketogluconate | − | − | w | − | − | − | − |
| Alkaline phosphatase | w | + | + | + | − | + | + |
| Acid phosphatase | w | w | − | − | − | + | − |
| Naphtol-AS-BI-phosphohydrolase | + | − | − | + | + | + | + |
| α-Glucosidase | − | − | + | − | − | − | − |
| N-acetyl-β-glucosaminidase | + | + | + | − | − | − | − |
| α-Mannosidase | − | − | w | − | − | − | − |
| G + C content (mol %) | 50.5 | 51.2 | 41.4[b] | 45[c] | ND | ND | ND |

[a]Taxa: 1, strain YC7007; 2, strain YC7010[T]; 3, B. siamensis KACC 15859[T]; 4, B. methylotrophicus KACC 13105[T]; 5, B. subtilis subsp. inaquosorum KACC 17047[T]; 6, B. amyloliquefaciens subsp. plantarum KACC 17177[T]; 7, B. tequilensis KACC 15944[T].
+: positive; −: negative; w: weakly positive; ND: not determined.
Data for the related type strains are from this study unless indicated.
[b]Sumpavapol et al., 2010.

Referring to Table 1, as a result of comparing physiological and biochemical features of YC7007 strain with those of other similar *Bacillus* species, it could be confirmed that YC7007 strain was different from the allied species in terms of growth at pH 4.5 and pH 12, growth in a 14% saline solution, growth at 60° C., gelatin degradation, carboxymethyl cellulose undegradation, degradation of arbutin, dilactose, starch, glycogen or gentibios in an API kit test, important phenotypic properties of naphthol-AS-BI-phosphohydrolase, N-acetyl-beta-glucose aminidase enzyme, or the like.

Figure 1B:
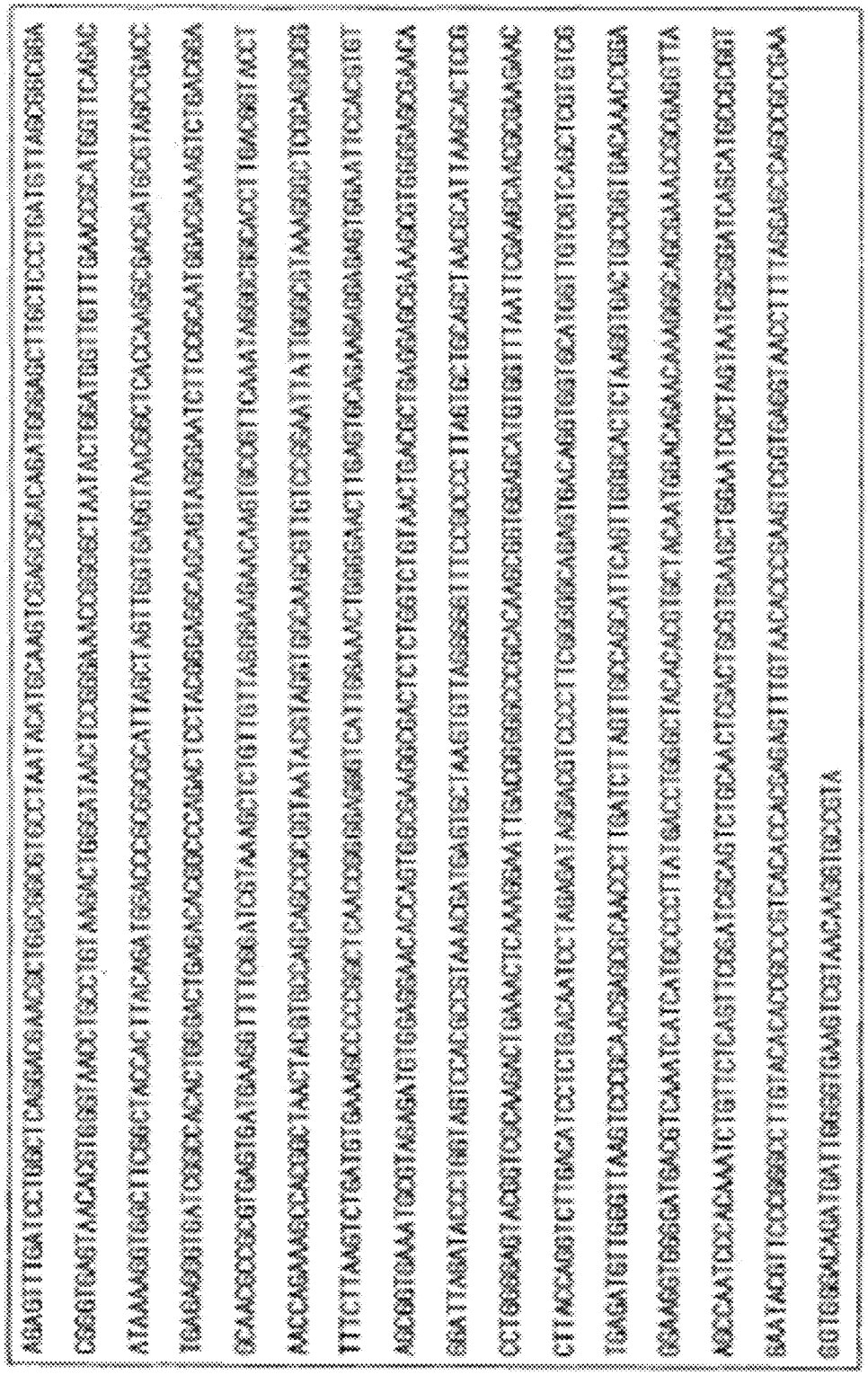
Figure 2:
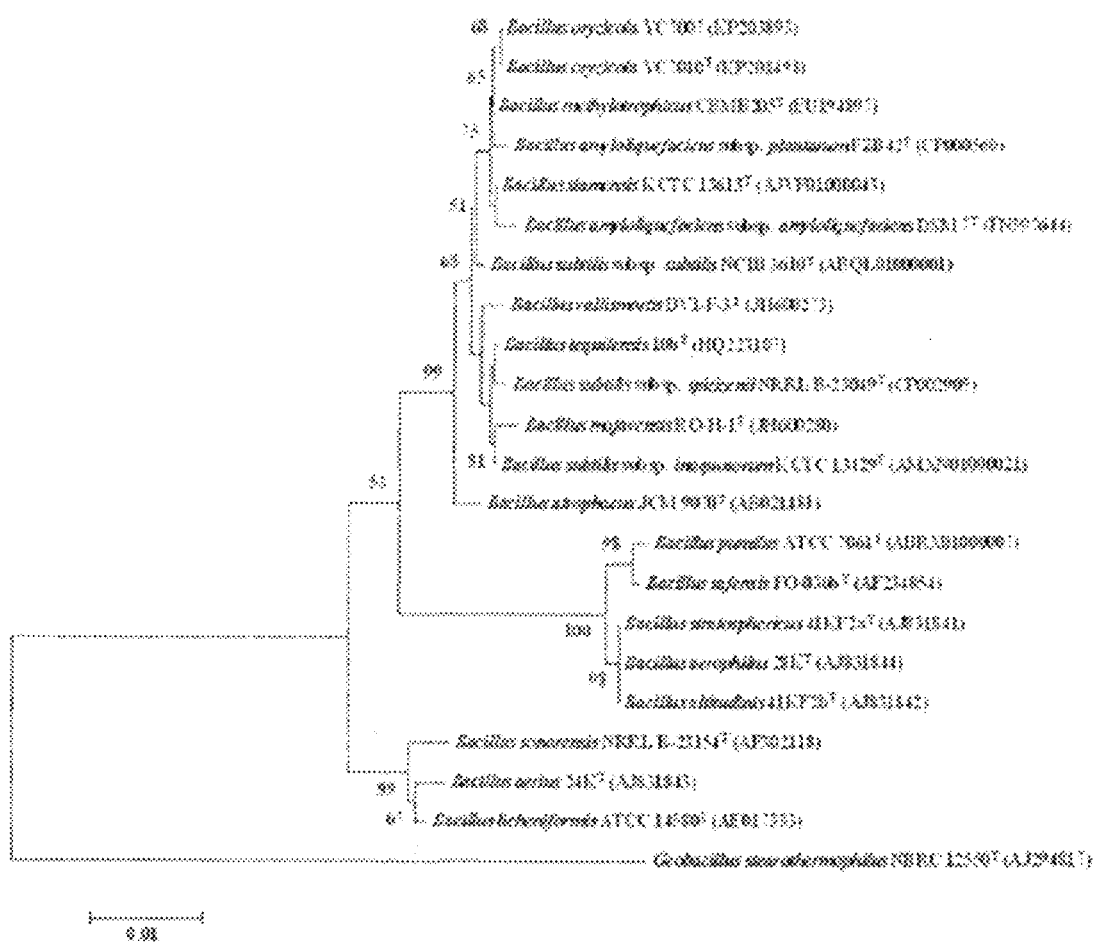
FIG. 2 is a view illustrating a phylogenetic tree formed by analysis of 16S rRNA gene sequence of YC7007 strain.

Meanwhile, after determining a base sequence of 16 16S rRNA gene in YC7007 strain (1513 bp, see FIGS. 1(a) and 1(b)), a systematic location of the base sequence was examined by executing homology search, compared to the database of GenBank/EMBL/DDBJ. FIG. 2 illustrates a phylogenetic tree formed by analysis of 16S rRNA gene sequence of YC7007 strain. In FIG. 2, the number of intersection points expresses a bootstrap value resulting from 1000 replicates.

In order to confirm a difference between YC7007 strain and allied species, DNA-DNA hybridization was investigated, and results thereof are shown in Table 2 below. The experiment was executed using a DIG DNA Labeling and Detection kit (Roche Applied Science) and with reference to the article of Lee et al. (Lee, S. H., Shim, J. K., Kim, J. M., Choi, H. K. & Jeon, C. O. (2011). *Henriciella litoralis* sp. nov., isolated from a tidal flat, transfer of *Maribaculum marinum* Lai et al. 2009 to the genus *Henriciella* as *Henriciella aquimarina* nom. nov. and emended description of the genus *Henriciella*. Int J Syst Evol Microbiol 61: 722-727). The extracted gene DNA (genomic DNA) was diluted at different concentration and a sodium hydroxide (NaOH) solution was added thereto, followed by applying heat at 80° C. to denaturize the genes. Thereafter, the denaturized gene was repeatedly attached three replicates to a Hybond-N+ nylon membrane (Amersham Pharmacia Biotech). After treating the same with a restriction enzyme HaeIII, the treated DNA fragments were used as a labeled DNA probe for cross-hybridization between strains. Temperatures for hybridization and washing were used according to indication manuals. Random primed DNA labeled with digoxigenin (DIG)-dUTP and hybrids was detected on the nylon membrane by enzyme immunoassay using a DIG High Prime DNA Labeling kit (Roche Applied Science). Hybridization signals were determined and analyzed using a scanner (HP Scanjet 3770) and Adobe Photoshop (v. 7.0). 100% of hybridization signal of target DNA and probe was caught. A DNA-DNA relatedness value between strains was calculated from an intensity of self-hybridization signal through dilution. As a result, although the relatedness value of YC7007 strain to YC7010 strain was 91.5%, YC7007 strain exhibited a relatedness value of 50.4% or less compared to other species such as *B. amyloliquefaciens*, *B. methylotrophicus*, *B. siamensis*, *B. subtilis*, *B. tequilensis*. Therefore, this strain was confirmed as a different one from the above species. That is, only when such DNA-DNA relatedness value between similar species is 70% or higher, these species are recognized as the same species as each other. If the above value is less than the above level, such species are considered as different ones (Goris, J., Konstantinidis, K. T., Klappenbach, J. A., Coenye, T., Vandamme, P., and Tiedje, J M. (2007). DNA-DNA hybridization values and their relationship to whole-genome sequence similarities. Int J Syst Evol Microbiol 57:81-91).

TABLE 2

| Strain | DNA-DNA relatedness value (%) |
|---|---|
| YC7010 | 91.5 ± 11.0 |
| B. amyloliquefaciens subsp. plantarum KACC17177[T] | 41.9 ± 7.9 |

TABLE 2-continued

| Strain | DNA-DNA relatedness value (%) |
|---|---|
| B. methylotrophicus KACC 13105[T] | 48.7 ± 9.4 |
| B. siamensis KACC 15859[T] | 50.4 ± 3.5 |
| B. subtilis subsp. inaquosorum KACC 17047[T] | 47.4 ± 4.0 |
| B. requilensis KACC 15944[T] | 37.9 ± 5.7 |

Analysis of fatty acids between YC7007 strain and allied species was executed, and results thereof are shown in Table 3 below. Referring to Table 3, YC7007 strain had an overall pattern similar to the allied species, however, $C_{16:1}$ ω7c alcohol and $C_{16:1}$ ω11c were not found, and an amount of other fatty acids was a little different from the allied species.

TABLE 3

| Fatty acid | 1 | 2 | 3 | 4 | 5 |
|---|---|---|---|---|---|
| $C_{12:0}$ | 1.7 | — | — | — | — |
| $C_{14:0}$ | — | 1.1 | 1.1 | — | 0.7 |
| $C_{15:0}$ | — | — | — | — | 8.2 |
| $C_{16:0}$ | 6.1 | 7.7 | 4.1 | 5.1 | 3.3 |
| $C_{17:0}$ | — | — | — | — | 0.9 |
| $C_{18:0}$ | — | 5.1 | 1.1 | — | — |
| iso-$C_{14:0}$ | 4.6 | 2.9 | 2.6 | 6.1 | 2.7 |
| iso-$C_{15:0}$ | 28.1 | 27.7 | 31.9 | 28.8 | 30.7 |
| iso-$C_{16:0}$ | 6.8 | 5.2 | 3.9 | 5.9 | 2.5 |
| iso-$C_{17:0}$ | 6.4 | 6.4 | 7.6 | 6.9 | 5.6 |
| iso-$C_{17:1}$ ω 10c | 2.0 | 1.7 | 2.6 | — | 1.6 |
| anteiso-$C_{15:0}$ | 38.4 | 32.0 | 35.6 | 39.8 | 37.2 |
| anteiso-$C_{17:0}$ | 5.9 | 5.3 | 5.8 | 7.6 | 4.7 |
| $C_{16:1}$ ω 7c alcohol | — | 3.4 | 1.2 | — | — |
| $C_{16:1}$ ω 11c | — | 1.4 | 1.5 | — | 2.0 |
| $C_{20:1}$ ω 7c | — | 0.2 | — | — | — |
| Summed feature 4* | — | — | 1.1 | — | — |

Figure 3:
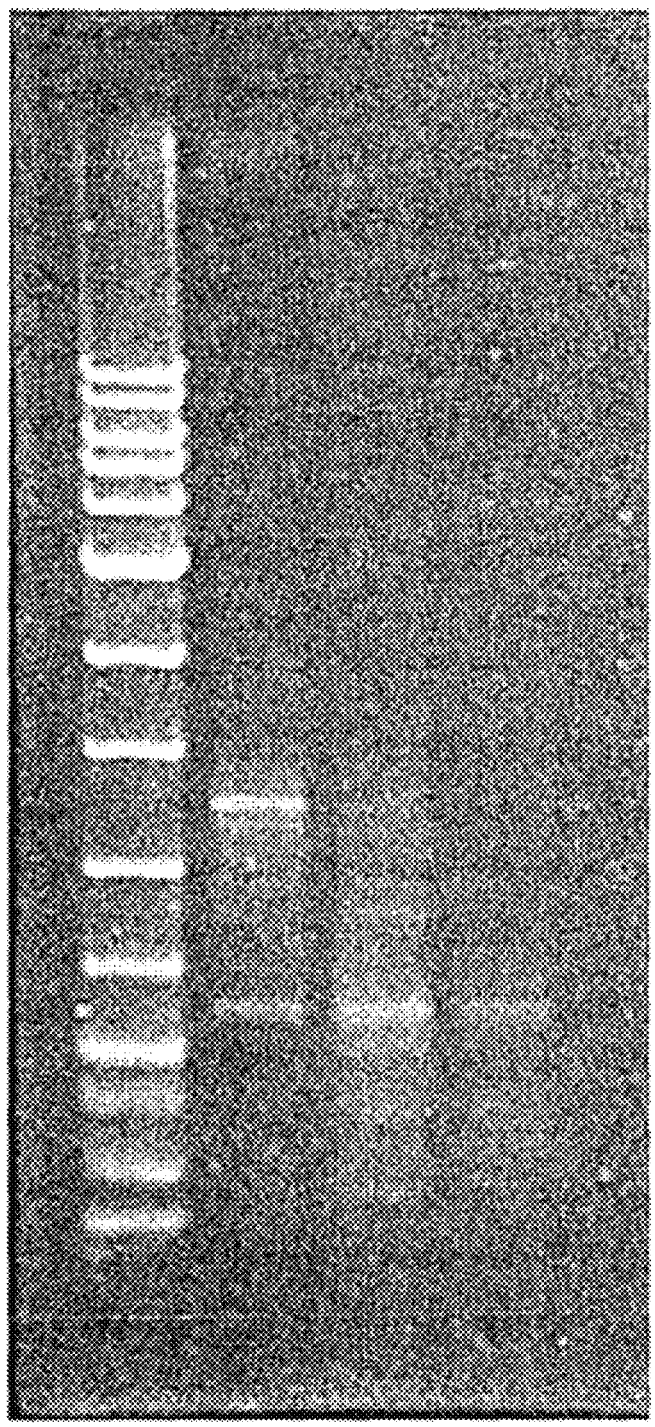
FIG. 3 a photograph illustrating analyzed results of YC7007 strain through genetic analysis, that is, BOX-PCR, compared to similar strains.

[Note]
Summed features include $C_{17:1}$ ISO I/ANTEI not analyzed by gas chromatography
1: YC7007
2: YC7010[T]
3: B. amyloliquefaciens subsp. plantarum KACC 17177[T]
4: B. methylotrophicus KACC13105[T]
5: B. siamensis KACC 15859[T]
—: not found FIG. 3 illustrates comparison and analysis results of YC7007 strain, compared to the allied species through gene analysis (BOX-PCR). A polymerase for the gene analysis (BOX-PCR) was Platinum Taq DNA polymerase High Fidelity (Invitrogen), while using BOXAR1 (5'-CATCG-GCAAGGCGACGCTGACG-3') as a primer. PCR conditions included an initial denaturation at 95° C. for 7 minutes, denaturation, annealing and extension at 90° C. for 30 seconds, 40° C. for 1 minute and 72° C. for 3 minutes, respectively, which are a series of 35 replicates processes, and the final extension was executed by reacting the strain at 72° C. for 10 minutes to amplify the gene. The resulting PCR product was subjected to determination of the amplification using 1% LE agarose gel (Seakem). In FIG. 3, M denotes 1 kb marker, 1 denotes YC7007 strain, 2 denotes Bacillus methylotrophicus KACC13105 strain, and 3 denotes Bacillus siamensis PD-A10[T] strain, respectively.

As shown in FIG. 3, in order to compare YC7007 strain in detail with a standard strain having the same scientific name as that of YC7007 strain, the gene analysis (BOX-PCR) was executed. As a result, it became clear that YC7007 strain was different from the allied species.

Accordingly, in review of the physiological and biochemical, and molecular biological results obtained above, the microorganism of the present invention has been determined as a novel strain, named Bacillus oryzicola YC7007 strain, which was duly deposited with Korean Culture Center of Microorganisms (KCCM) (having the address of KCCM, 361-221, Yurim B/D, Hongje-1-dong, Seodaemun-gu, Seoul 120-091, Republic of Korea) under the Accession number of KCCM11275P on Apr. 18, 2012. The deposit has been made under the terms of the Budapest Treaty and all restrictions imposed by the depositor on the availability to the public of the biological material will be irrevocably removed upon the granting of a patent.

A taxonomical description for a novel Bacillus oryzicola would be given as follows.

The above bacterium is a gram-positive and aerobic bacterium able to form an endophytic spore (0.6-1.0×2.5-2.8 μm), of which cells exist alone or in a pair. When the bacterium was cultured on $\frac{1}{10}$ TSA medium for 24 hours, a bacteria flora has a creamy white color and is formed to be convex at a center thereof while having a regular edge form. This bacterium may be grown at a temperature of 20 to 60° C., pH 4.5 to pH 12 and a NaCl concentration of 0 to 13%. As a result of the antibiotic-resistance test, it could be found that the present bacterium has resistance to 30 μg/ml concentration of chloramphenicol, however, not exhibiting resistance to 10 μg/ml ampicillin, gentamicin and penicillin as well as 30 μg/ml tetracycline, streptomycin, vancomycin and kanamycin. Major fatty acids are anteiso-$C_{15:0}$ and iso-$C_{15:0}$.

Assay of Inhibitory Efficacy of YC7007 Strain to Pathogenic Fungi and Bacteria in an Incubator In order to examine inhibitory efficacy of including 10 species of isolation endophytic bacteria including YC7007 strain to pathogenic fungi and bacteria, antibacterial activity was investigated as follows.

The antibacterial activity of endophytic bacteria YC7007 was determined by investigating the growth inhibition according to confrontation bioassay to 4 species of important plant pathogenic fungi (Gibberella fujikuroi (bakanae), Pythium ultimum (damping-off), Bipolaris oryzae (brown spot of rice), Magnaporthe grisea (rice blast)) and 3 species of (Burkholderia glumae (grain rot), Xanthomonas oryzae pv. oryzae, Xanthomonas oryzae pv. oryzae (bacterial blight)).

The pathogenic fungi and YC7007 strain were subjected to investigation into growth inhibitory effects by a paper disc method in ⅕ PDA and $\frac{1}{10}$ TSA growth media including 5 g of potato agar sugar medium (PDB, Difco) (16 g agar/1 l distilled water), respectively. The paper disc (a diameter of 5 mm) was placed at an equal distance of 1 cm from the periphery of an incubator, and after sufficiently permeating the paper disc with 100 μl of strain culture solution, a disc (6 mm) having pathogenic fungal hypha grown for 4 days in a PDA medium was placed at the center thereof, followed by culturing at 24 to 28° C. for 4 to 6 days in accordance with pathogens.

Investigation into inhibition of pathogenic bacteria was executed by suspending the pathogenic bacteria cultured at 28° C. overnight in sterilized and distilled water ($O.D._{600}$=0.1) and smearing 0.1 ml of the suspension on a medium, followed by measuring a pathogen growth inhibitory degree of YC7007 strain. Pathogen inhibitory effects of a culture filtrate produced by YC7007 strain were determined using a filtrate prepared by conducting a shaking culture on a culture liquid medium excluding agar at 28° C. for 72 hours (120 rpm), centrifuging the culture solution and filtering the same through a Millipore filter. In order to monitor a reaction to a temperature of the culture filtrate, after treating in a warm water kept at respective treatment temperatures for 10 minutes, such inhibitory effects were investigated.

The following table 4 illustrates results of the investigation into antibacterial activity of YC7007 strain to major plant pathogenic fungi and major plant pathogenic bacteria.

and such plant diseases subjected were rice blast, rice sheath blight, tomato gray mold rot, tomato late blight (pathogen: *Phytophthora infestans*), wheat leaf rust (pathogen: *Puccinia recondita*), barley powdery mildew (pathogen: *Blumeria graminis* f. sp. *hordei*) and red pepper anthracnose (pathogen: *Colletotrichum coccodes*), etc.

TABLE 4

| | Inhibition distance (mm) | | | | | | |
|---|---|---|---|---|---|---|---|
| Strain | *Burkholderia glumae* | *Xanthomonas oryzae* pv. *oryzae* | *Xanthomonas oryzae* pv. *oryzicola* | *Gibberella fujikuroi* | *Bipolaris oryzae* | *Magnaporthe grisea* | *Pythium ultimum* |
| YC7005 | − | +++ | +++ | +++ | +++ | +++ | +++ |
| YC7007 | ++++ | ++++ | ++++ | +++ | ++++ | ++++ | ++++ |
| YC7008 | − | +++ | +++ | +++ | +++ | +++ | +++ |
| YC7009 | − | +++ | +++ | +++ | +++ | +++ | +++ |
| YC7010 | ++++ | ++++ | ++++ | +++ | ++++ | ++++ | ++++ |
| YC7011 | − | − | − | ++ | ++ | ++ | ++ |
| YC7012 | ++ | ++ | ++ | +++ | +++ | +++ | +++ |
| YC7021 | − | − | − | − | ++ | ++ | ++ |
| YC7024 | − | − | − | +++ | +++ | +++ | +++ |
| YC7026 | − | nt | nt | +++ | +++ | +++ | +++ |

[Note]
− inhibition distance: +, <3 mm; ++, 4-5 mm; +++, 6-8 mm; ++++, >8 mm.

Referring to Table 4, it could be seen that, although antibacterial activity of the endophytic bacteria YC7007 strain to plant pathogenic fungi is a little varied depending on the medium, hypha growth inhibitory effects of 3 to 10 mm were exhibited.

Further, referring to Table 5, it could be seen that the culture solution showed growth inhibitory effects of 4 to 10 mm while the culture filtrate showed growth inhibitory effects of 3 to 8 mm, at the antibacterial activity 1/10 TSA of the endophytic bacteria YC7007 strain to plant pathogenic bacteria.

TABLE 5

| | Inhibition degree | | | |
|---|---|---|---|---|
| Culture | *Burkholderia glumae* | *Xanthomonas oryzae* pv. *Oryzae* | *Pectobacterium carotovorum* | *Pseudomonas syringae* |
| Culture solution | ++++ | ++++ | +++ | ++ |
| Culture filtrate | +++ | +++ | + | + |

[Note]
− Inhibition distance:
+, <3 mm;
++, 4-5 mm;
+++, 6-8 mm;
++++, 8-10 mm

From the above results, it could be understood that the present strain has broader and superior pathogen inhibitory effects over any other antagonistic bacteria known up to now.

Assay of Pot Test Pesticide Control Efficacy of YC7007 Strain to Pathogenic Fungi Based on the inhibitory effect in the test inside an experimental incubator according to Example 2, investigation into pesticide control effects of YC7007 strain to seven (7) species of major plant diseases was executed by directly treating the corresponding plants with YC7007 strain. The control efficacy assay was requested to and executed by the Korea Research Institute of Chemical Technology (KRICT), Treatment was executed by placing two pots of each plant disease on a rotational disc 1 day before inoculation with YC7007 suspension, and spraying the suspension over the plant by means of a spray gun (1 kg/cm$^2$) while rotating the disc to homogeneously adhere the suspension throughout the plant. Investigation into disease-resistance inducing effects by drenching the strain suspension was executed by drenching 5 ml of the strain per three pots of each host plant 7 days before inoculation of pathogens, cultivating the host plant in a greenhouse for 1 week, and then, examining a degree of disease attack. The strain suspension was prepared and used by shake-culturing the strain in 1/10 TSB medium at 28° C. overnight, centrifuging the same, and then, suspending bacteria cells in a 10 mM $MgSO_4$ solution to adjust a concentration thereof to $2\times10^6$ cfu/ml. Investigation of pathogen inoculation and disease attack was executed by inoculating 7 species of pathogen spores and hyphae to the respective host plants. Specific experimental procedures of the respective plant diseases are performed as described below.

Rice blast (RCB) was prepared by inoculating a rice bran agar medium with a pathogen, *Magnaporthe grisea* (*M. grisea*) KJ201 strain, culturing the same in an incubator at 25° C. for 2 weeks to form a spore, and then, cultivating the same in sterilized and distilled water to provide a spore suspension with a predetermined concentration ($3\times10^5$ spores/ml). The prepared RCB was sufficiently sprayed enough to flow down medicated NakDong rice (a period of 3 to 4 main leaves). The inoculated rice was cultured in a dark state in a humid room for 24 hours and subjected to disease attack in an air-conditioned room with a relative humidity of 80% or more at a temperature of 26° C. for 4 days, followed by investigation into an infected leaf area ratio.

Rice sheath blast (RSB) was prepared by entering a desired amount of bran in a 1 l culture bottle, sterilizing and inoculating the same with a pathogen, *Rhizoctonia solani* (*R. solani*) AG1 strain, and then, culturing the treated product in an incubator at 25° C. for 7 days. Disease inoculation was executed by grinding the cultured hypha mass into small pieces, uniformly inoculating a pot of medicated and grown NakDong rice a period of 4 to 5 leaves with the ground pieces, and culturing the same in a humid room (25° C.) for 7 days to cause the disease attack, followed by investigation into the infected leaf area ration formed in the sheath.

Tomato gray mold rot (TGM) was prepared by inoculating a potato agar medium with a pathogen, *Botrytis cinerea* (*B. cinerea*), culturing the same in a thermostat at 25° C. to form a spore and use the same as an inoculant. Pathogen inoculation was executed by culturing a spore, adjusting the concentration thereof to $3\times10^5$ spores/ml using a hemocytometer, and then, spray-inoculating a medicated tomato young plant (a period of 2 to 3 leaves). The inoculated tomato young plant was placed in a humid cabinet at 20° C. (with a relative humidity of 95% or more) to induce disease attack for 3 days, followed by investigation into an infected leaf area ratio.

Tomato late blight (TLB) was prepared by inoculating an oatmeal medium with a pathogen, *Phytophthra infestans* (*P. infestans*) strain and culturing the same in an incubator at 20° C. to form a zoosporangium. Pathogen inoculation was executed as follows: adding the formed zoosporangium to sterilized and distilled water, cultivating the same, and then, preparing a spore suspension with a spore concentration of $3\times10^4$ sporocyst/ml; holding the prepared suspension in a refrigerator to chill the same and leak swam spores, thereby preparing a swam spore suspension; and spray-inoculating a medicated tomato young plant (a period of 2 to 3 leaves) with the prepared suspension. The pathogen-inoculated tomato young plant was subject to dew treatment in a humid room at 20° C. for 2 days, and then, subjected to disease attack in an air-conditioned room, followed by investigation into the infected leaf area ratio occurred on the leaves 3 days after the inoculation.

Wheat leaf rust (WLR) has a pathogen, *Puccinia recondita* (*P. recondita*), as a biotroph. Therefore, the inoculant used herein was a uredospore formed in a wheat young plant while directly sub-culturing the same on a plant in a laboratory. In order to investigate medicinal effects of the strain, 5 grains of wheat seeds (plant variety: Eunpa) were seeded in a disposable pot (diameter: 4.5 cm), cultivated in a greenhouse for 8 days to form one leaf young plant, followed by medicating the young plant and spray-inoculating the same with an inoculant (0.11 g/l of spores). The inoculated wheat young plant was subjected to dew treatment in a humid room at 20° C. for 1 day, and then, moved to an air-conditioned room with a relative humidity of 70% at 20° C. to induce disease attack, followed by investigation into the infected leaf area ratio 7 days after the inoculation.

Barley powdery mildew (BPM) has a pathogen, *Bluemeria graminis* (*B. graminis* f. sp. *hordei*) as a biotroph. Therefore, the inoculant used herein was a spore formed in the barley while sub-culturing the barley young plant in a laboratory. In order to investigate medicinal effects of the strain, 5 grains of barley seeds (plant variety: winter barley) were seeded in a disposable pot (diameter: 4.5 cm), cultivated in a greenhouse for 8 days to form 1 leaf stage young plant, followed by spraying a medicine over the young plant, wind-drying the same in the greenhouse and scattering powdery mildew spores over the medicated barley to inoculate the same. The inoculated barley young plant was kept in an air-conditioned room with a relative humidity of about 60% at 20 to 23° C. to cause the disease attack for 7 days, followed by investigation into an infected leaf area ratio.

Red pepper anthracnose (RPA) was prepared by inoculating an oatmeal medium with a pathogen, *Coletotricum cocodes* (*C. coccodes*), culturing the same at 25° C. for 10 days to form spores, cultivating the same, adjusting a concentration thereof to reach $2\times10^5$ spores per ml, thereby providing a spore suspension. The medicated chili pepper young plant (at a period of 3 to 4 leaves) was spray-inoculated with the prepared spore suspension, placed in a humid room (25° C.), and subjected to dew treatment for 2 days to disease attack in an air-conditioned room (25° C., 75% RH). Three days after the inoculation, followed by investigation into an infected leaf area ratio.

A control value was calculated from the infected leaf area ratio obtained by investigation of disease according to the following Equation 1.

$$\text{Control value (\%)} = (1 - \text{infected leaf area ratio in a treated group/infected leaf area ratio in an untreated group}) \times 100 \quad \text{[Equation 1]}$$

The following Table 6 illustrates results of the investigation into control effects of YC7007 strain to major plant diseases.

TABLE 6

| | Control value (%) | | | | | | |
|---|---|---|---|---|---|---|---|
| Treatment method | Rice blast | Rice sheath blight | Tomato gray mold rot | Tomato late blight | Wheat leaf rust | Barley powdery mildew | Anthracnose |
| Foliar spraying | 70 | 6 | 36 | 31 | 83 | 72 | 71 |
| Soil drenching | 35 | 0 | 0 | 0 | 0 | 0 | 0 |

Referring to Table 6, with regard to the control effects to 7 species of major plant disease, it could be seen that, in a case of rice blast, wheat leaf rust, barley powdery mildew and red pepper anthracnose, the control value ranged from 70 to 83%, whereas rice sheath blight, tomato gray mold rot and tomato late blight showed a low control value of 36% or less. In particular, the control effect by inducing disease-resistance after soil drenching was 35% in a case of the rice, therefore, it was confirmed that YC7007 strain has host-specific property to the rice.

Assay of Grain Rot Prevention Efficacy by Inducing Disease-Resistance by YC7007 Strain In order to examine rice grain rot prevention efficacy by inducing disease-resistance by YC7007 strain, investigation into the control effect was executed as follows.

After transplanting a rice young plant (DongJin 1) cultivated in a plant growth cabinet (28 to 30° C., relative humidity of 80% or more) for 5 weeks into sterilized or non-sterilized bed soil for rice cultivation, 10 ml of strain suspension ($2\times10^7$ cfu/ml) was immediately distributed thereon (120 g). YC7007 strain suspension was prepared by shake-culturing in 1/10 TSB medium at 28° C. overnight, centrifuging the same, suspending bacteria cells in a 10 mM $MgSO_4$ solution, and then, properly adjusting a concentration thereof. 5 days after the treatment, inoculation was executed by smearing an inoculation probe with a rice grain rot pathogen (*B. glumae*) suspension ($5\times10^7$ cfu/ml, $OD_{600}$=0.1) and inoculating 20 leaves with three replicates for each treatment. The pathogen suspension was centrifuged after culturing for 24 hours in a R2A medium, and bacteria cells were suspended in the 10 mM $MgSO_4$ solution and used by properly adjusting a concentration thereof. After the inoculation of pathogen, the treated product was placed on the growth cabinet for 5 days, and then, investigated for a degree of necrosis of infected leaf. The degree of disease attack was classified into 0 to 3 (0: no sign of disease, 1: small necrotic spot, 2: large brown spot formed of several necrotic spots, 3: necrosis over an entire area), and a control value was estimated by calculating a disease inhibitory degree compared to the control group. A control group agent for induction of rice disease-resistance used herein was a 1 mM benzothiadiazole (BTH) solution.

Figure 4:
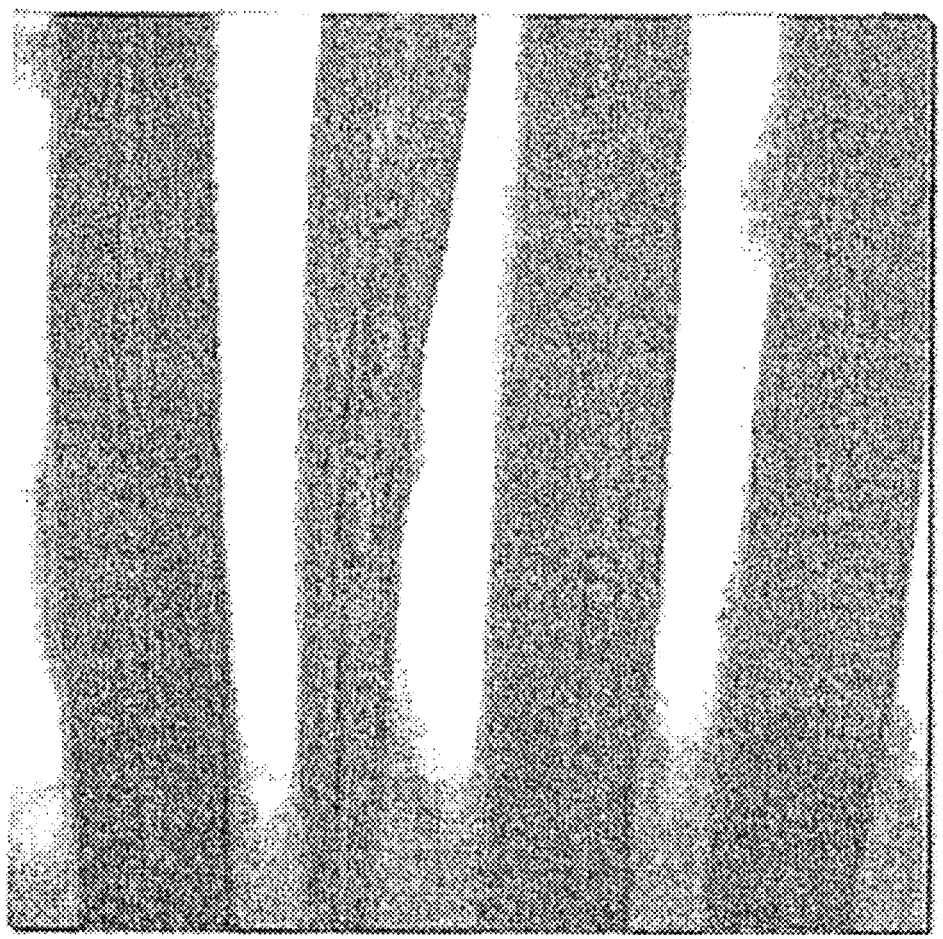
FIG. 4 is a photograph illustrating for distinction and comparison of treatments to explain a rice grain rot prevention effect.

The following Table 7 illustrates results of the investigation into rice grain rot prevention effects by soil treatment using YC7007 strain, and FIG. 4 is a photograph illustrating for distinction and comparison of treatments to explain the rice grain rot prevention effects.

TABLE 7

| Treatment | Degree of disease attack | | Control value (%) |
|---|---|---|---|
| | Length of infected leaf (mm) | Disease attack degree | |
| Non-treatment | 0 ± 0c | 0 ± 0c | — |
| B. glume | 17.4 ± 1.0a | 2.4 ± 0.06a | — |
| YC7007 + B. glume | 2.0 ± 0.2b | 1.10 ± 0.06b | 54 |
| BTH | 1.5 ± 0.2bc | 1.03 ± 0.09b | 57 |

Referring to Table 7 and FIG. 4, it was demonstrated that, as a result of inoculating soil with pathogens 5 days after the treatment of the soil with YC7007 strain suspension and investigating the control effect, the strain-treated group had an infected leaf length of 2.0 mm and a disease attack degree of 1.1 while a control group treated using only the pathogens had an infected leaf length of 17.4 mm and a disease attack degree of 2.4, thus exhibiting considerably reduced values compared to the control group. Further, the control value was 54% generally similar to 57% in a case of BTH as the control group agent, thus demonstrating the same range of host disease-resistance inducing effects.

Assay of Bacterial Blight Prevention Efficacy by Inducing Disease-Resistance by YC7007 Strain In order to examine bacterial blight prevention efficacy by inducing disease-resistance of YC7007 strain, investigation into the control effect was conducted as follows.

After transplanting a rice young plant (DongJin 1) cultivated in a plant growth cabinet (28 to 30° C., relative humidity of 80% or more) for 5 weeks into sterilized or non-sterilized bed soil for rice cultivation, 10 ml of strain suspension ($2\times10^7$ cfu/ml) was immediately distributed thereon (120 g). 5 days after the treatment, inoculation was executed by smearing an inoculation probe with a bacterial blight pathogen (*X. oryzae* pv. *oryzae*) suspension ($1\times10^7$ cfu/ml, $OD_{600}$=0.1) and inoculating 20 leaves with three replicates for each treatment. The bacterial blight pathogen suspension was prepared by the same procedures as described for the rice grain rot above. After the inoculation of pathogen, the treated product was placed on the growth cabinet for 5 days, and then, investigated for a degree of necrosis of infected leaf. The degree of disease attack was classified into 0 to 9 (0: no sign of disease, 1: small necrotic spot, 2 to 4: middle-sized brown spot consisting of several necrotic spots, 5 to 8: large brown spot consisting of several necrotic spots, 9: necrosis over an entire area), and the control value was estimated by calculating a disease inhibitory degree compared to the control group.

Figure 5:
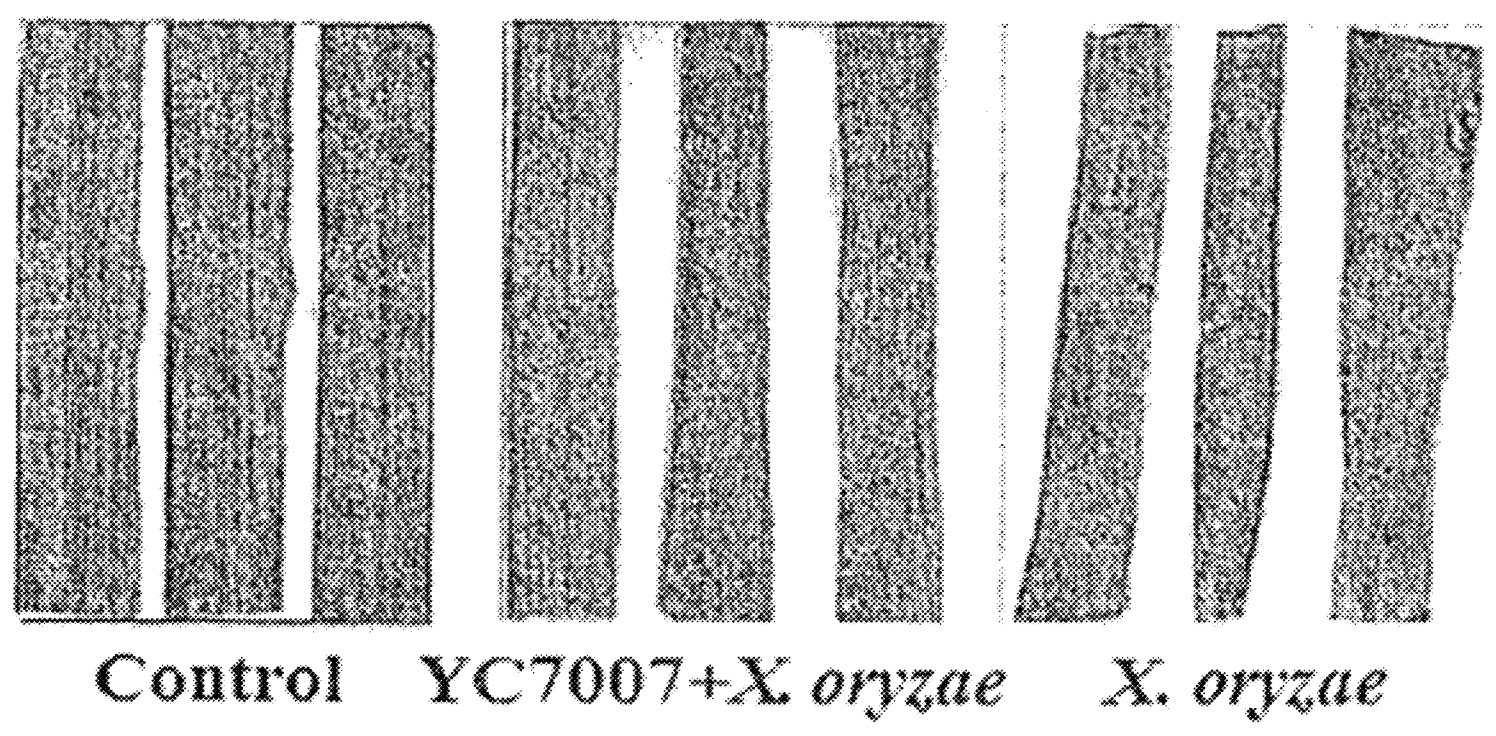

The following Table 8 illustrates results of the investigation into bacterial blight prevention effects by soil treatment using YC7007 strain, and FIG. 5 is a photograph illustrating for distinction and comparison of treatment to explain rice bacterial blight prevention effects.

TABLE 8

| Treatment Pathogen | Disease attack degree* | | Control value (%) |
|---|---|---|---|
| inoculation method | Pin prick | clipping | |
| Non-treatment | 1.0 ± 0c | 1.0 ± 0c | — |
| X oryzae | 7.4 ± 0.4a | 2.4 ± 0.06a | — |
| YC7007 + X oryzae | 2.3 ± 0.67b | 2.2 ± 0.23b | 65 |

*the disease attack degree ranges from 0 to 9; other English characters mean that a significant difference may occur by Dunkin's multi-verification (p = 0.05)

Referring to Table 8 and FIG. 5, it was demonstrated that, as a result of inoculating soil with pathogens 5 days after the treatment of the soil with YC7007 strain suspension and investigating the control effect, although there was a little difference between pin prick type and clipping type inoculations, the YC7007 strain-treated group had disease attack degrees of 2.3 and 2.2, respectively, compared to the control group treated using only the pathogens that had disease attack degrees of 7.4 and 5.67, respectively, thus exhibiting high control values of 69% and 61% (average 65%), respectively. Consequently, excellent host disease-resistance inducing effects were confirmed.

Assay of Bakanae Prevention Efficacy by Inducing Disease-Resistance by YC7007 Strain In order to examine bakanae prevention efficacy by inducing disease-resistance of YC7007 strain, investigation into the control effect was conducted as follows.

After transplanting a rice young plant (DongJin 1) cultivated in a plant growth cabinet (28 to 30° C., relative humidity of 80% or more) for 2 weeks into sterilized or non-sterilized bed soil for rice cultivation, 15 ml of strain suspension ($10^5$ to $10^7$ cfu/ml) was immediately distributed thereon (150 g). 3 days after the treatment, inoculation was executed by repeatedly inoculating the young plants three replicates such that 10 young plants per each repeat are inoculated with 1.5 g/pot of bakanae pathogen (*G. fujikuroi*) ($5\times10^5$ cfu/g). After the inoculation of pathogen, the treated product was placed on the growth cabinet for 10 to 30 days, and then, investigated for a degree of necrosis of infected leaf. The degree of disease attack was classified into 0 to 5 (0: no sign of disease, 1: slightly yellowed leaf and twisted stem, 2 to 4: yellowed leaf and tall stem, 5: necrosis over an entire area), and the control value was estimated by calculating a disease inhibitory degree compared to the control group.

The following Table 9 illustrates results of the investigation into bakanae prevention effects by soil treatment using YC7007 strain

TABLE 9

| Treatment | Disease attack degree* | Control value (%) |
|---|---|---|
| Non-treatment | 0 ± 0c | — |
| G. fujikuroi | 3.40 ± 0.31a | — |
| YC7007 + G. fujikuroi | 1.40 ± 0.12b | 58.8 |

*the disease attack degree ranges from 0 to 5; other English characters mean that a significant difference may occur by Dunkin's multi-verification (p = 0.05)

Referring to Table 9, it was demonstrated that, as a result of inoculating soil with pathogens 3 days after the treatment of the soil with YC7007 strain suspension and investigating the control effect, the control group treated using only the pathogens that had a disease attack degree of 3.4, whereas the strain-treated group had a disease attack degree of 1.4, thus exhibiting a control value of 58.8%. Consequently, excellent host disease-resistance inducing effects were confirmed.

Assay of Rice Growth Promoting Efficacy by Treatment Using YC7007 Strain

In order to examine rice growth promoting efficacy by YC7007 strain treatment, investigation into plant growth promoting efficacy was executed as follows.

After uniformly mixing 1 kg of rice cultivation soil with 200 ml of strain suspension (2×10$^7$ cfu/ml), germinated rice seeds were sowed therein. After sowing, growth degree of stems and roots were investigated after 10 days (seedling stage), 30 days (tillering stage) and 75 days (booting stage), respectively, while cultivating the rice seeds in a plant growth cabinet (28 to 30° C., relative humidity of 80% or more). As a control group, soil mixed with the same amount of 10 mM MgSO$_4$ buffer solution only was used. In order to maintain a density of the bacteria 30 days after the inoculation and during the tillering stage, 5 ml of YC7007 strain suspension was again drenched in the soil at the rice root part. Each treatment was repeated three times, and 10 plants were used per each repeat.

The following Table 10 illustrates results of the investigation into rice growth promoting efficacy by YC7007 strain.

TABLE 10

| | Growth state | | | | | |
|---|---|---|---|---|---|---|
| | Seedling stage | | Tillering stage | | Booting stage | |
| Tretment | Stem (cm) | Root (cm) | Stem (cm) | Tiller number | Stem (cm) | Tiller number |
| Non-treatment | 11.7 ± 0.3b | 2.7 ± 0.3b | 36.5 ± 1.2b | 1.9 ± 0.2b | 55.3 ± 0.3b | 5.3 ± 0.7b |
| YC7007 | 19.3 ± 0.3a | 7.7 ± 0.3a | 46.3 ± 2.0a | 2.9 ± 0.1a | 61.0 ± 2.0a | 7.0 ± 0.6a |

(*) Other English characters mean that a significant difference may occur by Dunkin's multi-verification (p = 0.05)

Referring to Table 10, it was demonstrated that, as a result of treating the rice cultivating bed soil with YC7007 strain, cultivating the same in a pot and investigating the growth promoting effects in each growth time period, the YC7007 strain-treated group had considerably longer lengths of stem and root of 19.3 cm and 7.7 cm in the seedling stage, than 11.7 cm and 2.7 cm of the untreated group. Similarly, the stem length in the tillering stage was more increased by 27.4% and the tiller number was also greater by about 52%. Further, during the booting stage, the YC7007 strain-treated group showed 10.8% more increased stem length and greater tiller number by about 32%. Consequently, rice growth promoting efficacy by YC7007 strain treatment was confirmed.

Investigation of Production and Effects of Pathogen Inhibitory Antibacterial Material In order to confirm that the inhibition of pathogens by YC7007 strain occurs by the production of antibacterial material, whether the antibacterial material is produced in 1/10 TSB liquid medium or not was investigated. A degree of antibacterial material inhibitory effect was determined by measuring a growth inhibition distance of fungal hypha or bacteria cells formed around a paper disc according to a disc diffusion method. After shake-culturing YC7007 strain in a liquid medium at 28° C. (180 rpm) for 72 hours and centrifuging at 9000 g for 10 minutes, a culture filtrate was filtered through a Millipore filter (0.2 μm), followed by determining antibacterial activity in each culture time.

Figure 6A:
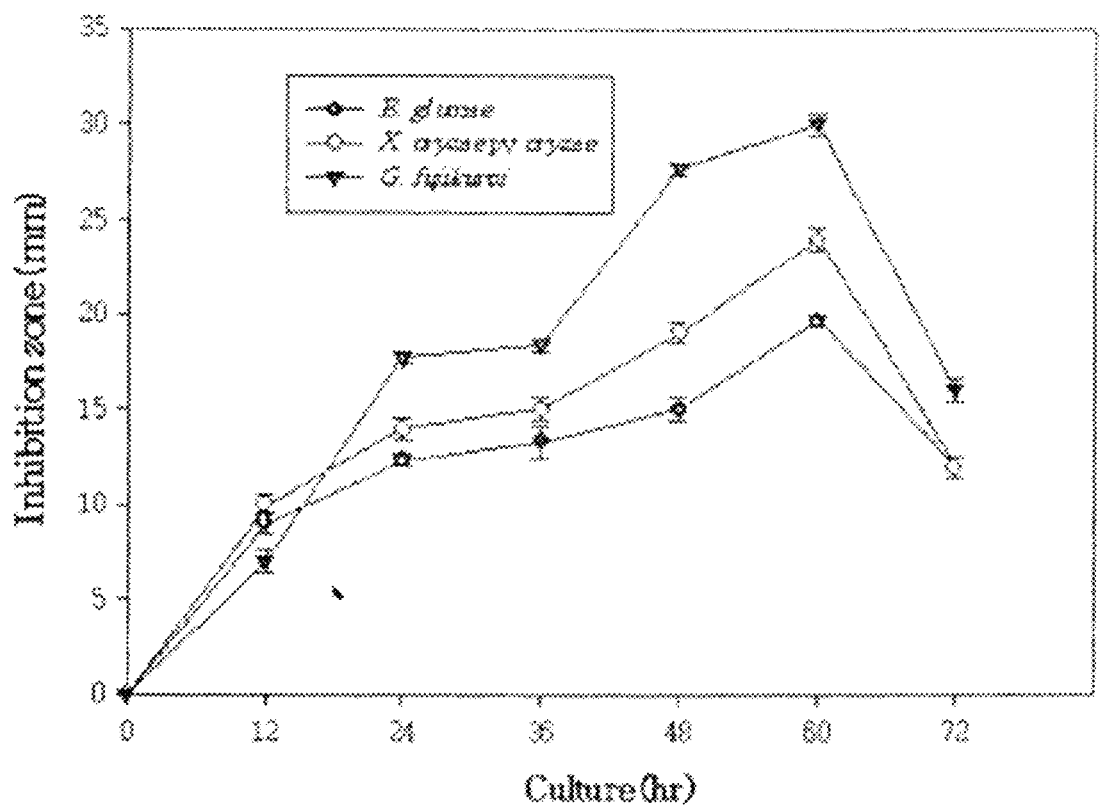
FIG. 6(*a*) is a graph and FIG. 6(*b*) is a photograph illustrating antibacterial effects of a YC7007 strain culture solution in each culture time period.
Figure 6B:
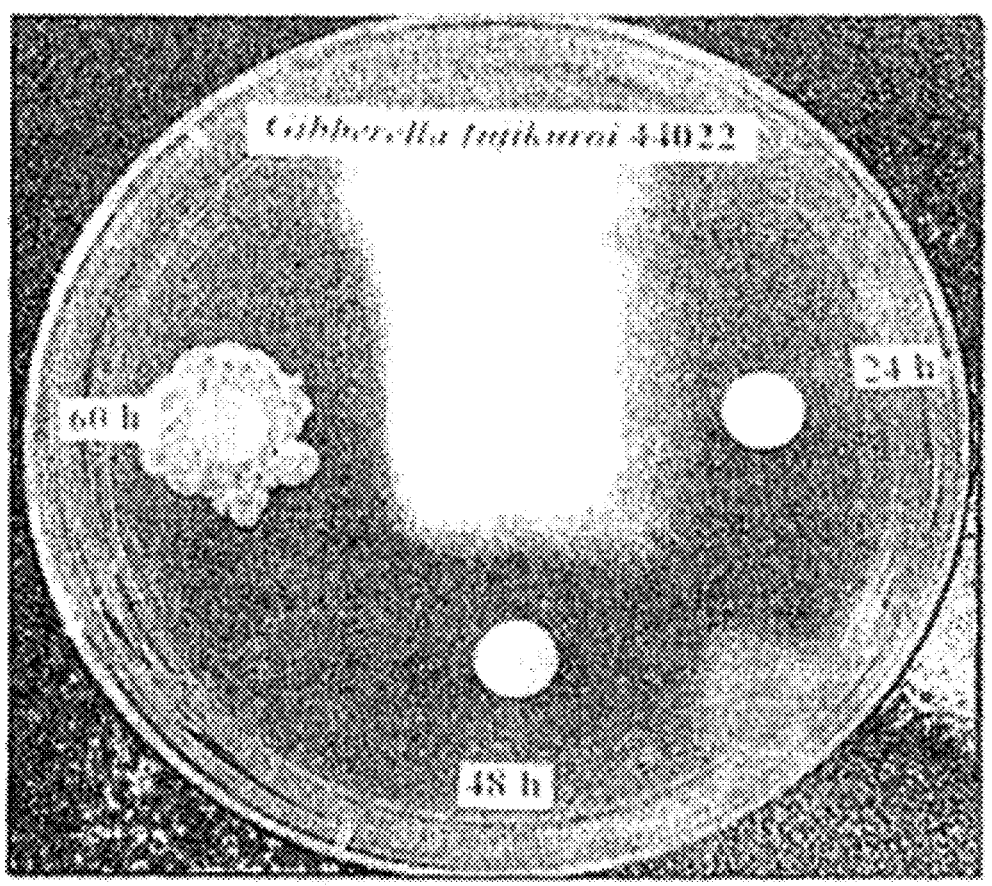
Figure 7:
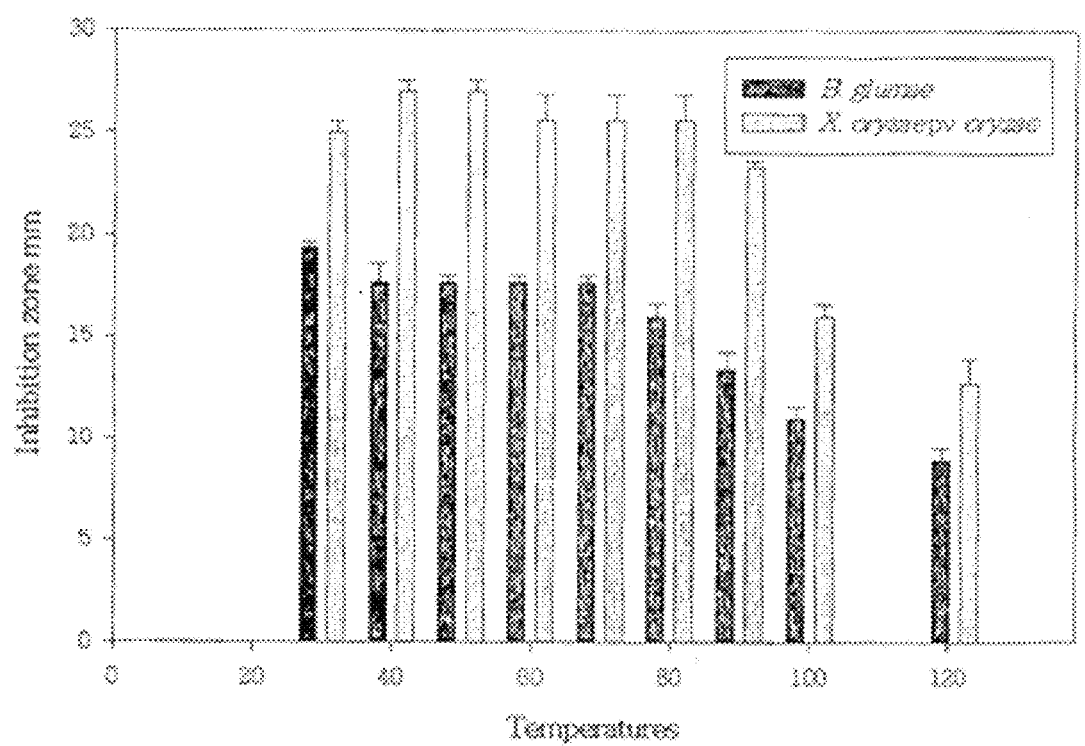
FIG. 7 is a graph illustrating antibacterial effects of a YC7007 strain culture solution in each treatment temperature.

FIG. 6(a) is a graph and FIG. 6(b) is a photograph illustrating antibacterial effects of a YC7007 strain culture solution in each culture time period, while FIG. 7 is a graph illustrating antibacterial effects of a YC7007 strain culture solution in each treatment temperature.

First, referring to FIGS. 6(a) and 6(b), with regard to antibacterial effects of the strain culture filtrate in each culture time period, it could be seen that, in a case of the rice pathogen bacteria (B. glume, X. oryzae) and bakanae bacteria (G. fujikuroi), the inhibitory effect is raised as the strain culture time is increased, therefore, the most excellent inhibitory effect was achieved in the culture filtrate for 60 hours. However, it was demonstrated that the effect was sharply decreased in the culture filtrate for 72 hours.

Further, referring to FIG. 7, as a result of investigating stability of the culture filtrate to heat, antibacterial activity was maintained until the treatment at 90° C., however, the inhibitory effect was a slightly reduced if the temperature exceeds 100° C. From this result, it could be understood that the antibacterial material produced by YC7007 strain may be relatively stable to heat.

Formulation of YC7007 Strain

In order to maintain the activity of YC7007 strain and a density during storage, the YC7007 strain was formulated in forms of powders and liquid as follows.

A bacterial culture solution obtained by incubating the strain in a large size of fermenter (1 ton or more) or a fungus body obtained after centrifugation was mixed with any clay mineral such as kaolin, bentonite, peat, etc. in a ratio of 1:100, dried at a low temperature, and then, homogeneously ground to prepare a solid material in a powder form. At the same time, the fungi culture product was mixed with the clay mineral in a ratio of 1:100 to also prepare a liquid suspension form.

As a result of examining the density of the formulated sample as described above, it was found that most of the formulations included the strain in an amount of 10$^8$ cfu/g or more, and the liquid suspension mixed and formulated with the clay mineral had a density of $10^8$ cfu/ml or more.

Example 2

It is presumed that rice is the staple food of more than half the world's population and has been produced in about 745 million tons in 2013. The rice is mostly produced in Asian region, however, due to diseases as a main restriction reason, involves loss of 24 to 41% every year (Annonymous 2014. Rice market monitor. In: *Monthly report, Food and Agriculture Organization of the United Nations*, vol. 17, iss. 1, pp 1-4(http://www.fao.org/3/a-i3735e.pdf); Savary, S., Willocquet, L., Elazegui, F. A., Castilla, N. P. and Teng, P. S. 2000. Rice pest constrainsts in tropical Asia: Quantification of yield losses due to rice pests in a range of production situations. Plant Dis. 84:357-369.). With regard to the rice, at least 70 types of diseases caused by fungi, bacteria, virus and nematodes have been reported. In particular, rice blast, bacterial leaf blight, grain rot and bakanae are most serious seed infectious diseases to reduce an amount of harvest (Ou, S. H. 1985. Rice disease. 2nd ed. Commonwealth Mycol. Inst., 361 pp. Key, England.). For instance, bacterial blight caused by *Xanthomonas oryzae* pv. *oryzaet* could reduce 10 to 50% of total rice production depending on circumstance, thus to expert a strong influence on society (Mew, T. W. 1992. Foliar disease, bacterial blight. In: *Compendium of Rice Diseases*, eds. by R. K. Webster and P. S. Gunnell, pp. 10-11.). Alternatively, other bacterial diseases such as seedling blight and rot, leaf sheath rot, leaf browning, panicle blight, bacterial wilt and grain rot caused by *Burkholderia glumae* may sometimes reduce even 75% of yield (Croplife 2015. Bacterial panicle blight, the disease with the greatest impact on rice crops. (http://www.croplifela.org/en/disease-of-the-month.html?id=182); Kim, J., Kang, Y., Kim, J. G., Choi, 0. and Hwang, I. 2010. Occurrence of *Burkholderia glumae* on rice and field crops in Korea. Plant Pathol. J. 26:271-272; Ura, H., Furuya, N., Iiyama, K., Hidaka, M., Tsuchiya, K. and Matsuyama, N. 2006. *Burkholderia gladioli* associated with symptoms of bacterial grain rot and leaf-sheath browning of rice plants. J. Gen. Plant Pathol. 72:98-103.). Further, a reduction of yield due to bakanae caused by *Fusarium fujikuroi* is estimated to about 10 to 50% in rice cultivation area of Asian region (Bonman, J. M. 1992. Root and crown disease, bakanae. In: *Compendium of Rice Diseases*, eds. by R. K. Webster and P. S. Gunnell, p. 27.). For pesticide control of the above diseases, chemical bactericides have been broadly used in most of Asian countries for last several tens years, however, efficacy of the bactericides has recently decreased due to an occurrence of tolerance (Yang, Y. R., Kim, Y. C., Lee, S. W., Lee, S. W., An, G. G. and Kim, I. S. 2012. Involvement of an efflux transporter in prochloraz resistance of *Fusarium fujikuroi* CF245 causing bakanae. J. Korean Soc. Appl. Biol. Chem. 55:571-574.). Further, misuse of the chemical bactericides may induce adverse effects to agricultural environments and workers. Accordingly, developing a novel pesticide control means capable of replacing the above chemical bactericides has been attempted, in particular, in Asian countries where biological control using antagonistic bacteria (Gnanamanickam, S. S. 2009. An overview of progress in biological control. In: *Biological control of rice diseases, Progress in biological control*, ed. by S. S. Gnanamanickam, vol. 8, pp. 43-51. Springer, Netherlands.).

The biological control using antagonistic bacteria may be embodied by means of environmentally safe and integrated disease management. Diverse microorganism genuses such as *Bacillus, Burkholderia, Lysobacter, Pantoea, Pseudomonas* and *Streptomyces* have been used as biological formulations for a lot of agricultural crop diseases. However, with regard to the biological control of rice diseases, only several studies have been reported (Bouizgarne, B. 2013. Bacteria for plant growth promotion and disease management. In: *Bacteria in agrobiology, Disease management*, ed. by D. K. Maheshwari, pp. 15-34. Springer-Verlag, Berlin, Heidelberg; McSpadden Gardener, B. 2010. Biocontrol of plant pathogens and plant growth promotion by *Bacillus*. In: *Recent developments in management of plant diseases, Plant pathology in the 21st Century*. eds. by U. Gisi, I. Chet and M. L. Gullino, chapt. 6, pp. 71-79. Springer-Amsterdam.). Multiuse of antatonistic bacteria *Streptomyces* and *Bacilluswas* has been attempted for control of rice sheath blight (Sung, K. C. and Chung, Y. R. 1997. Enhanced suppression of rice sheath blight using combination of bacteria which produce chitinases or antibiotics. In: *Proceedings of the 4th international workshop on plant growth promoting rhizobacteria present status and future prospects*, eds. by A. Ogoshi, K. Kobayashi, Y. Homma, F. Kodama, N. Konodo and S. Akino, pp. 370-373. OECD, Paris.). Rice blast and sheath blight were effectively prevented by *Bacillus vallismortis* EXTN-1 and two antagonistic bacteria, that is, *Pseudomonas fluorescens* mc75 and pc78 were effectively prevented (Choi, G. J., Kim, J. C., Park, E. J., Choi, Y. H., Jang, K. S., Lim, H. K., Cho, K. Y. and Lee, S. W. 2006. Biological control activity of two isolates of *Pseudomonas fluorescens* against rice sheath blight. Plant Pathol. J. 22:289-294; Park, K. S., Paul, D. and Yeh, W. H. 2006. *Bacillus vallismortis* EXTN-1 mediated growth promotion and disease suppression in rice. Plant Pathol. J. 22:278-282.). Bakanae and seedling rot of rice were also prevented by *Fusarium moniliforme, F. fujikuroi*, and antagonistic bacteria such as *P. fluorescens* and *Bacillus cereus* (Kazempour, M. N. and Elahinia, S. A. 2007. Biological control of *Fusarium fujikuroi*, the causal agent of bakanae disease by rice associated antagonistic bacteria. Bulg. J. Agric. Sci. 13:393-408; Rosales, A. M. and Mew, T. W. 1997. Suppression of *Fusarium moniliforme* in rice by rice-associated antagonistic bacteria. Plant Dis. 81:49-52.). Among diverse antagonistic bacteria, different *bacillus* species have been developed as commercially available biopesticides. The reason of such development is that the *bacillus* species could produce endospores and be sustained in natural environments for a long period of time after treatment (Hu, X., Roberts, D. P., Maul, J. E., Emche, S. E., Liao, X., Guo, X., Liu, Y., McKenna, L. F., Buyer, J. S. and Liu, S. 2011. Formulations of the endophytic bacterium *Bacillus subtilis* Tu-100 suppress *Sclerotinia sclerotiorum* on oilseed rape and improve plant vigor in field trials conducted at separate locations. Can. J. Microbiol. 57:539-546.).

*Bacillus* species widely used in biological control of many plant diseases in other hosts may include, for example, *Bacillus amyloliquefaciens, Bacillus subtilis, Bacillus pasteurii, B. cereus, Bacillus pumilus, Bacillus mycoides* and *Bacillus sphaericus* (Kloepper, J. W., Ryu, C. M. and Zhang, S. 2004. Induced systemic resistance and promotion of plant growth by *Bacillus* spp. Phytopathology 94:1259-1266; McSpadden Gardener, B. 2010. Biocontrol of plant pathogens and plant growth promotion by *Bacillus*. In: *Recent developments in management of plant diseases, Plant pathology in the 21st Century*. eds. by U. Gisi, I. Chet and M. L. Gullino, chapt. 6, pp. 71-79. Springer-Amsterdam.). It was proved that *B. subtilis* GB03 and *B. amyloliquefaciens* IN937 could prevent a bacterial pathogen, that is, *Erwinia carotovora* subsp. *Carotovora* in *Arabidopsis* (Ryu et al., 2004). Further, *B. cereus* AR156 and *B. subtilis* were proved to induce tolerance and control *Pseudomonas syringae* pv. tomato DC3000 in *Arabidopsis* (Niu, D. D., Liu, H. X., Jiang, C. H., Wang, Y. P., Wang, Q. Y., Jin, H. L. and Guo, J. H. 2011. The plant growth promoting rhizobacterium *Bacillus cereus* AR156 induces systemic resistance in *Arabidopsis thaliana* by simultaneously activating salicylate- and jasmonate/ethylene dependent signaling pathways. *Mol. Plant-Microbe Interact.* 24:533-542.). Some of these *bacillus* species have specific characteristics in aspects of antifungal properties, antibacterial properties, plant growth promotion and tolerance inducing activities (Park, K. S., Paul, D., Kim, J. S. and Park, J. W. 2009. L-alanine augments Rhizobacteria induced systemic resistance in cucumber. *Folia Microbiol.* 54:322-326; Ryu, C, M. 2013. Promoting plant protection by root-associated microbes. *Plant Pathol. J.* 29:123-124.). Different *Bacillus* species have been isolated from diverse land plants and halophytes, and some of those exhibit endogeneity (see Non-Patent Document 7). The *bacillus* genus includes 299 species at present, and more than 30 novel species have been reported for last 5 years on the basis of a multiphase study including 16S rRNA gene sequence, DNA-DNA hybridization assay, fatty acid profile, and physical and biochemical experiments (LPSN. 2015. *List of prokaryotic names with standing in nomenclature.* (http://www.bacterio.net/*bacillus*.html)).

In the present example, with regard to two different *bacillus* strains YC7007 and YC7010 isolated from rice roots, development of new biological pesticide formulations having multifunctional activity was discussed, and classification thereof has been characterized according to a multiphase approach. Further, control efficacy of novel YC7007 and YC7010 strains has been investigated through not only the promotion of rice growth but also the induction of tolerance against bacterial blight and panicle blight.

Material and Method (1) Isolation and Culture of Endophytic Bacteria

From roots of the rice collected from a rice paddy soil in the farm of Gyeongsang National University (Jinju city, Korea), endophytic bacterial strains were isolated. In order to isolate the strains, a sample piece was washed with flowing water several times, subjected to surface sterilization with 70% ethanol for 5 minutes, with a 1.2% sodium hypochlorite (NaOCl) for 10 minutes. Lastly, the sample was washed with sterilized and distilled water several times. For confirming the sterilization, the washed fragment was placed in 1/10 TSA (one-tenth strength tryptic soy broth agar) at 28° C. for 3 days, and then, bacteria growth was observed. After confirming no existence of bacteria colony, a sample fragment was again sterilized with 70% ethanol for several seconds, the height pressure sterilized water was fed into a high pressure sterilizer, and then, ground by means of a sterilized bowl and a mortar (see Non-Patent Document 7). A part of the liquid containing the ground fragment was diluted with the high pressure sterilized water by 10 times in order, followed by placing a part thereof (0.1 ml) in 1/10 TSA medium supported with cycloheximide and culturing the same on a plate at 30° C. for 3 days. The bacteria colony grown on the medium was selected based on a clear form of colony. The bacterial strain purely isolated was subcultured in 1/10 TSA medium and stored at −70° C. for subsequent use. In order to conduct the bacterial strain culture, a medium including 10 g of protease peptone, 10 g of yeast extract, 4 g of ammonium chloride, 4 g of magnesium sulfate, 10 g of glucose and 15 g of agar per liter of distilled water was prepared.

(2) Antagonistic Activity to Fungal and Bacterial Pathogens

With regard to endophytic bacteria, experiments using major plant fungal pathogens such as *Alternaria panax* KACC 42461, *F. fujikuroi* KACC 44022, *F. oxysporum* KCTC 16909, *Sclerotinia sclerotiorum* GSCC 50501, *Pythium ultimum* GSCC 50651, *Bipolaris oryzae* KACC 40853, *Botrytis cinerea* KCTC 6973, *Magnsporthe grisea* KACC 40415, *Botryosphaeria dothidea* GSCC 50201, and *Rhizoctonia solani* KCTC 40101 were executed. Antagonistic activity of the bacterial strain was assessed by measuring a hypha growth inhibitory area of a fungal pathogen in a potato dextrose agar (PDA) medium using an in vitro control living test (see Non-Patent Document 7). For antibacterial experiment, *B. glumae* KACC10359 and *X. oryzae* pv. *Oryzae* KACC 10208 were grown in R2A (one-half strength R2A) and YGC media (10 g glucose, 30 g $CaCO_3$, 5 g yeast extract and 15 g agar per liter distilled water), respectively, an experiment for inhibitory activity was executed by a diffusion paper disc method. A culture filtrate of bacterial strain YC7007 was prepared from the culture solution at another culture time by ultrafiltration through centrifugation (5,000 g, 10 minutes) and a Millipore filter (0.2 μm).

(3) Assay of Induction-Resistance to Bacterial Pathogen

For the induction of resistance of YC7007 species to bacterial blight and panicle blight caused by *X. oryzae* pv. *Oryzae* KACC 10208 and *B. glumae* KACC10359, respectively, a pot test was executed. After surface sterilization of a rice seed *Oryza sativa* L. cultivar DongJin in 1.2% sodium hyperchlorite solution for 10 minutes and in 70% ethanol for 5 minutes, respectively, the sterilized rice seed was rinsed with sterilized and distilled water three times and stored in a dark room at 30° C. for 3 days for germination, and the water was changed everyday. The germinated seed was sowed in nursery soil (Dasuran Sangto, Youngnong Sun Up, Korea), and then, placed in a greenhouse for cultivation. Thereafter, 2-weeks old rice sprouts were transplanted in a plastic pot (9.5×8×7 $cm^3$) including 150 g of soil that was sterilized under high pressure at 121° C. for 2 days at a rate of 20 minutes one day. In order to prepare a bacterial suspension of YC7007, bacterial cells were cultured in a liquid mass culture (160 rpm, 28° C.) for 2 days, followed by centrifugation (5,000 g, 10 minutes), and then, the suspension was taken and was adjusted to become different concentrations (5.6×10$^5$, 3.6×10$^6$, 2×10$^7$ CFU/ml) in a buffer (10 mM $MgSO_4$). While transplanting 2-weeks old rice, a cell suspension of YC7007 (15 ml) was drenched into a plastic pot including high pressure sterilized soil (150 g). YC7007 having an optimum concentration (2×10$^7$ CFU/ml) was used for an additional resistance inducing test in regard to the bacterial blight and panicle blight. A culture filtrate of YC7007 strain prepared from 60 h culture solution diluted by 10 times in 10 mM magnesium sulfate was injected on leaves until liquid drops have formed thereon, in order to investigate control effects. Then, 5 days after the YC7007 treatment, the bacterial pathogen was inoculated. The buffer was used as a control group and all experiments were conducted using 10 plants with three replicates for each treatment.

(4) Preparation of Inoculates for Bacterial Pathogens

As the inoculates of two bacterial pathogens, *B. glumae* KACC10359 and *X. oryzae* pv. *oryzae* KACC 10208 were prepared by culturing these in R2A and YGC media, respectively, on a rotational vibrator (160 rpm, 28° C.) and using a cell suspension. *B. glumae* culture solution was subjected to centrifugation (5,000 g, 10 minutes) and suspension of cell pellets in a buffer (10 mM $MgSO_4$) having an adjusted concentration of 6×10⁷ CFU/ml. For inoculation using *B. glumae* suspension, a biological assay, that is, pin-prick bioassay was executed. A bundle of 3 to 4 pins/needles was put into the suspension and leaves were picked out using the needles in the bundle. After inoculating 5-weeks old rice with the pathogen, a degree of disease attack was assessed at 5 day as follows. 0=no symptom, 1=slight infection but very little lesion, 2=entirely brown colored agglutinin lesion, 3=no description available (Cottyn, B., Cerez, M. T., Van Outryve, M. F., Barroga, J., Swings, J. and Mew, T. W. 1996. Bacterial diseases of rice. I. Pathogenic bacteria associated with sheath rot complex and grain discoloration of rice in the Philippines. *Plant Dis.* 80:429-437.). For the bacterial blight, the *X. oryzae* pv. *oryzae* suspension was prepared according to the same procedures as the case of *B. glumae.*, and had an adjusted concentration of $1.2 \times 10^7$ CFU/ml. A biological assay adopted for the bacterial blight was a clipping bioassay which is a method of cutting upper leaves using a pair of scissors containing the suspension. 7 days after the inoculation, a degree of disease attack was assessed according to 1 to 9-point method (Misra, J. K., Mew, T. W. and Merca, S. D. 1994. Field inspection. In: *A manual of rice seed health testing*, eds. by T. W. Mew and J. K. Misra, pp. 52-55. International Rice Research Institute, Philippines.). A reduction of disease (%) was calculated according to the following Equation 2.

Reduction of disease (%)=[(Disease attack degree of control group disease attack degree of treated group)/(Disease attack degree of control group)]×100 [Equation 2]

(5) Determination of Growth Promotion

Rice growth promotion by treatment using a cell suspension of YC7007 strain (2×10⁷ CFU/ml) was investigated over the period of cultivation. In a test tube (18 cm length) containing a medium (10 ml ½ MS media with 0.8% agar), a YC7007 cell suspension (1 ml) was drenched into a rhizosphere of the 5-weeks old rice. 7 days after the bacteria treatment, a growth degree was recorded (at day 12). For a pot test, the 2-weeks old rice was transplanted into a plastic pot including 150 g of high pressure sterilized soil and the bacteria suspension 15 ml, followed by drenching at day 7 after the transplantation. 9 days after the bacteria treatment, a growth degree was recorded (at day 30). Further, after drenching the bacteria suspension (15 ml) during the tillering stage (at day 30) and 40 days after the bacteria treatment from the tillering stage, a growth degree was recorded at the booting stage (at day 70). In the test tube and the pot test, the treatment was executed using 10 plants with three replicates for each treatment in order to conduct experiments of growth promotion activity. Herein, the buffer was used as a control group.

(6) Systematic Analysis Based on 16S rRNA Gene Sequence and DNA-DNA Hybridization Using primers (bacterial universal primers 27F and 1492R), 16S rRNA gene was amplified from genomic DNA extracted using a commercially available extraction kit (Intron Biotech, Seoul, Korea). A purified PCR product was subjected to sequencing (GenoTech Inc., Daejeon, Korea). (Lane, D. J. 1991. 16S/23S rRNA sequencing. In: *Nucleic acid techniques in bacterial systematics*, eds. by E. Stackebrandt and M. Goodfellow, pp. 115-175. Chichester: Wiley). In order to identify a systematic location of novel endophytic bacteria compared to other allied species, 16S rRNA gene sequence of the strain was compared to the existing sequences obtained from a database (NCBI and the EzTaxon-e database server) (Kim, O. S., Cho, Y. J., Lee, K., Yoon, S. H., Kim, M., Na, H., Park, S. C., Jeon, Y. S., Lee, J. H., Yi, H., Won, S. and Chun, J. 2012. Introducing EzTaxon-e: a prokaryotic 16S rRNA gene sequence database with phylotypes that represent uncultured species. *Int. J. Syst. Evol. Microbiol.* 62:716-721.). A multiple sequence alignment was executed using a CLUSTAL_X software (Thompson, J. D., Gibson, T. J., Plewniak, F., Jeanmougin, F. and Higgins, D. G. 1997. The CLUSTAL_X windows interface: flexible strategies for multiple sequence alignment aided by quality analysis tools. *Nucleic Acids Res.* 25:4876-4882.), and then, a gap therebetween was edited according to a BioEdit program (Hall, T. A. 1999. BioEdit: a user friendly biological sequence aligned editor and analysis program for Windows 95/98/NT. *Nucleic Acids Symp. Ser.* 41:95-98.). In order to form a phylogenetic tree with a bootsstrap value resulting from 1000 replicates, a neighbor-joining method (neighbor-joining method; Saitou, N. and Nei, M. 1987. The neighbor-joining method: a new method for reconstructing phylogenetic trees. *Mol. Biol. Evol.* 4:406-425.), maximum-parsimony (maximum-parsimony; Fitch, W. M. 1972. Toward defining the course of evolution: minimum change for a specific tree topology. *Syst. Biol.* 20:406-416.), maximum-likelihood algorithms in a MEGA 5.10 software (maximum-likelihood algorithms; Tamura, K., PetXSerson, D., Peterson, N., Stecher, G., Nei, M. and Kumar, S. 2011. MEGAS: molecular evolutionary genetics analysis using maximum likelihood, evolutionary distance, and maximum parsimony methods. *Mol. Biol. Evol.* 28:2731-2739.), etc. were used (Felsenstein, J. 1985. Confidence limits on phylogenies: an approach using the bootstrap. *Evolution* 39:783-791.). In order to determine a DNA-DNA relatedness value between strains DNA-DNA, DNA-DNA hybridization using a kit (DIG DNA labeling and detection kit, Roche Applied Science) was performed according to instructions of manufacturers as well as the above-described methods (Lee, S. H., Shim, J. K., Kim, J. M., Choi, H. K. and Jeon, C. O. 2011. *Henriciella litoralis* sp. nov., isolated from a tidal flat, transfer of *Maribaculam marinum* Lai et al. to the genus *Henriciella* as *Henriciella aquimarina* nom. nov. and emended description of genus *Henriciella*. *Int. J. Syst. Evol. Microbiol.* 61:722-727.).

(7) Morphological, Expressional and Chemical Classification Characteristics

A morphology of cells was observed by an optical microscope (Nikon, ×1000), and the existence of flagellum was observed by a transmission electron microscope (Hitachi, model H-600) using a cell culture solution grown in a R2A medium at 28° C. for 24 hours. Using a kit (bioMerieux Gram stain kit), gram reaction was investigated according to the instruction of a manufacturer. A hydrolysis experiment of the strain was executed using caseine, esculin, gelatin, starch, L-tyrosine, urea, Tween 20 and Tween 80 according to standard protocols (Smibert, R. M. and Krieg, N. R. 1994. Phenotypic characterization. In: *Methods for general and molecular bacteriology*, eds. by P. Gerhardt, R. G. E. Murray, W. A. Wood and N. R. Krieg, pp. 607-654. American Society for Microbiology, Washington, D.C.; Reichenbach, H. 1992. The order Cytophagales. In: *The Prokaryotes*, eds. by A. Balows, H. G. Truper, M. Dworkin, W. Harder and K. H. Schleifer, 2nd ed., vol. 4, pp. 3631-3675. Springer, New York.). With regard to enzyme activity, acid production from various carbohydrates, absorption of various strains and growth in carbohydrates, investigation was performed using commercially available systems (API ZYM, API 20E, API 20NE and API 50CH kits, respectively) at 28° C. according to the instructions of manufacturers (BioMerieux). Further, with regard to the growth at different temperatures and pH values (pH 4.0-14.0 at an interval of 0.5 pH units), investigation was executed after culturing in R2A culture solution using desired buffers for 5 days (Xu, P., Li, W. J., Tang, S. K., Zhang, Y. Q., Chen, G. Z., Chen, H. H., Xu, L. H. and Jiang, C. 2005. *Naxibacter alkalitolerans* gen. nov., sp. nov., a novel member of the family 'Oxalobacteraceae' isolated from China. *Int. J. Syst. Evol. Microbiol.* 55:1149-1153.). Further, after culturing at 28° C. for 5 days, salt-resistance was assessed using R2A culture solution supplemented with 1 to 14% sodium chloride (w/v, at an 1% interval). An experiment for duplicate antibiotic-sensitivity was executed using a variety of antibiotics (10 µg ampicillin, 30 µg chloramphenicol, 10 µg penicillin, 10 µg gentamycin, 3 µg kanamycin, 30 µg vancomycin, 30 µg streptomycin and 30 µg tetracycline) according to a disc diffusion method (filter-paper disc diffusion assays) (Yasir, M., Aslam, Z., Song, G. C., Jeon, C. O. and Chung, Y. R. 2010. *Sphingosinicella vermicomposti* sp. nov., isolated from vermicompost, and emended description of the genus *Sphingosinicella*. *Int. J. Syst. Evol. Microbiol.* 60:580-584.). Preparation of a cell wall and analysis of peptidoglycan were executed by a modified Schleifer method, wherein TLC was conducted using a cellulose sheet instead of paper chromatography (Schleifer, K. H. 1985. Analysis of the chemical composition and primary structure of murein. *Methods Microbiol.* 18:123-156.). In order to analyze cellular fatty acid, a bacterial strain was cultured in a R2A culture solution at 28° C. and microorganism cells were taken in a mid-exponential growth phase ($OD_{600}$=0.4-0.5). Analysis of fatty acid methyl esters was executed according to the instruction of a microbial identification system (MIDI; Microbial ID, Inc.). The extract was analyzed through GC (Agilent 6890), and fatty acid profiles were compared and identified using TSBA 40 database provided by a Sherlock software (ver. 4.0). Amino acids of an entire cell hydrolyte of the bacterial strain were extracted and analyzed by a method of Staneck and Roberts (Stanek, J. L. and Roberts, G. D. 1974. Simplified approach to identification of aerobic actinomycetes by thin-layer chromatography. *Appl. Microbiol.* 28:226-231.). Isoprenoid quinines were extracted and analyzed through reverse-phase HPLC by a method of Komagata and Suzuki (Komagata, K. and Suzuki, K. 1987. Lipid and cell-wall analysis in bacterial systematics. s19:161-207.). In order to measure G+C content of chromosome DNA, genomic DNA of YC7010 strain was extracted and purified by a method of Ausubel et al. (Ausubel, F. W., Brent, R., Kingston, R. E., Moore, D. D., Seidman, J. G., Smith, J. A. and Struhl, K. 1995. *Current Protocols in Molecular Biology*, New York: Wiley.), followed by measuring enzymatically decomposed nucleoside and G+C content through reverse-phase C18 column (Mesbah, M., Premachandran, U. and Whitman, W. B. 1989. Precise measurement of the G+C content of deoxyribonucleic acid by high-performance liquid chromatography. *Int. J. Syst. Bacteriol.* 39:159-167.). According to a modified method of Minnikin et al. (1984), polar lipid was extracted and isolated through TLC using Merck Kieselgel 60-HPTLC. Further, after spraying a ninhydrin solution (0.2% (w/v) solution of ninhydrin in butanol saturated with water) over a plate, the plate was heated at 105° C. for 10 minutes to detect amino-lipid (Ross, H. N. M., Grant, W. D. and Harris, J. E. 1985. Lipids in archaebacterial taxonomy. In: *Chemical Methods in Bacterial Systematics*, eds. by M. Goodfellow and D. E. Minnikin, pp. 289-300. Academic Press, London.). Further, phospholipid was detected by spraying a Zinzadze reagent of Dittmer and Lester (Dittmer, J. C. and Lester, R. L. 1964. A simple, specific spray for the detection of phospholipids on thin-layer chromatograms. *J. Lipid Res.* 15:126-127) over the plate. Further, glycolipid was detected by heating the same using 1-naphthol spray reagent for 3 to 5 minutes (Jacin, H. and Mishkin, A. R. 1965. Separation of carbohydrates on borate impregnated silica gel G plates. *J. Chromatogr.* 18:170-173.). The detection of phosphatidyl choline was conducted using a Dragendorff reagent (Sigma-Aldrich; St. Louis, Mo.). Further, a total lipid profile was detected by, after spraying a phosphomolybdic acid solution (Sigma-Aldrich; St. Louis, Mo.), heating the plate at 150° C. for 10 minutes.

(8) Statistical Analysis

In a case of in vitro analysis, a distribution-designed analysis with a completely randomized single element was employed to analyze data, while a completely randomized block design analysis was used in a case of in vivo analysis. Further, mean differences were compared by Duncan's method (Duncan's multiple range test (DMRT)). In all of these analyses, an SPSS software (ver. 17; SPSS Inc. in Chicago) was used.

Result of Experiment (1) Antagonistic Activity of Isolated Strain

Figure 8:
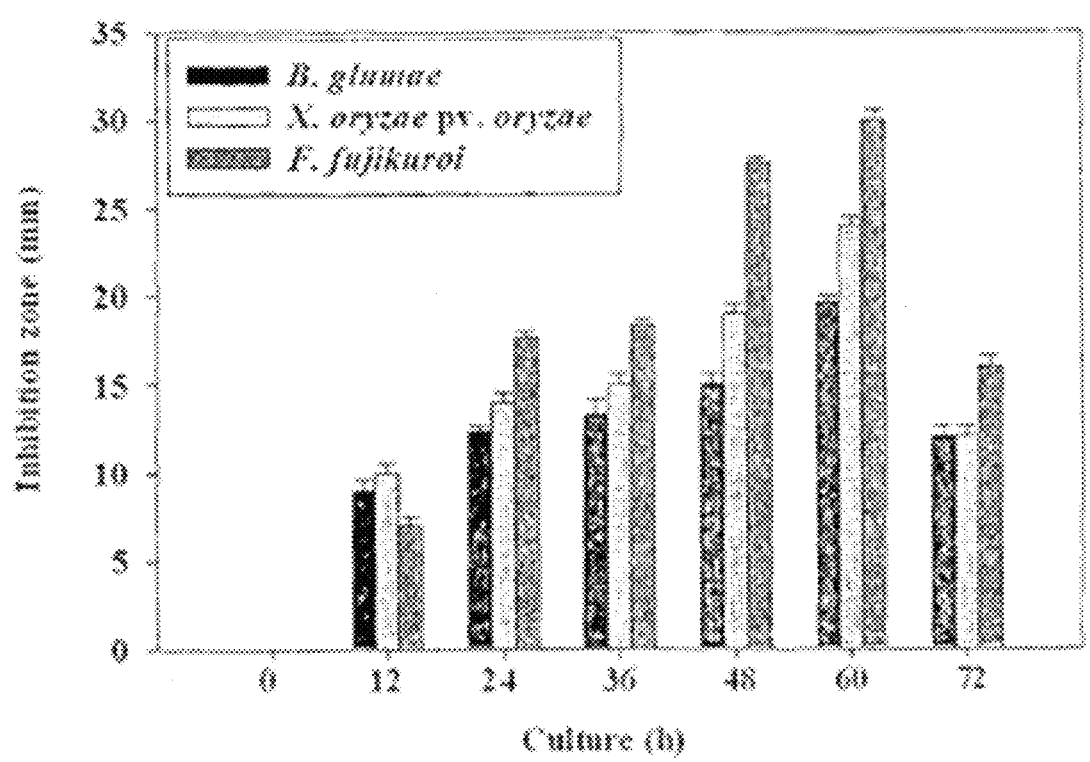
FIG. 8 is a graph illustrating growth inhibitory performances of the YC7007 strain culture solution in regard to major seed-borne bacterial pathogens.

It was demonstrated that, among 250 bacterial strains isolated from rice rhizosphere, 15 endophytic bacteria exhibit inhibitory activity to hypha growth of *F. fujikuroi* in a range of 2 to 20 mm or more. Based on 16S rRNA gene sequence, it was confirmed that such bacteria were associated with *Paenibacillus polymyxa*, *Bacillus siamensis*, *Paenibacillus jamilae*, *Bacillus methylotrophicus*, *Bacillus thuringiensis*, *B. cereus*, *Bacillus simplex* and *Bacillus daliensis*. These isolated bacteria were experimentally identified and belonged to allied genus because of similarity thereof ranging from 99.27 to 100%. In particular, among the isolated bacteria, two strains, that is, YC7007 and YC7010 had highest similarity to *B. siamensis*, thereby exhibiting strong antagonistic activity to *F. fujikuroi* (>20 mm inhibition zone) (see Table 11 below). Further, YC7007 showed strong antagonistic activity to alternative rice pathogens, that is, *B. oryzae*, *M. grisea*, *F. fukikuroi* and other major plant pathogens as well in a range of 10 to 29 mm inhibition zone on PDA (see Table 12 below). Further, a culture filtrate of YC7007 strain prepared at different cultivation times also exhibited favorable growth inhibitory ability to not only *F. fujikuroi* but also *B. glumae* and *X. oryzae* pv. *oryzae*, which are two major seed-derived bacterial pathogens (see FIG. 8). The culture filtrate of 60 h-old culture solution showed the strongest activity to *F. fujikuroi*, *X. oryzae* pv. *oryzae* and *B. glumae* in respective media, in the ranges of 30 mm, 24 mm and 19.7 mm inhibition zones, respectively.

TABLE 11

| Origin | Closely related strain | % Identity[a] | Inhibition[b] Fusarium fujikuroi |
|---|---|---|---|
| YC7005 | Paenibacillus polymyxa (AFOX01000032) | 99.77 | + |
| YC7006 | Paenibacillus polymyxa (AFOX01000032) | 99.77 | + |
| YC7007 | Bacillus siamensis (AJVF01000043) | 99.67 | ++++ |
| YC7008 | Paenibacillus polymyxa (AFOX01000032) | 99.27 | + |
| YC7009 | Paenibacillus jamilae (AJ271157) | 100 | + |
| YC7010[T] | Bacillus siamensis (AJVF01000043) | 99.67 | ++++ |
| YC7012 | Bacillus siamensis (AJVF01000043) | 99.60 | ++ |
| YC7013 | Bacillus methylotrophicus (EU194897) | 99.37 | ++ |
| YC7014 | Bacillus methylotrophicus (EU194897) | 99.62 | ++ |

TABLE 11-continued

| Origin | Closely related strain | % Identity[a] | Inhibition[b] Fusarium fujikuroi |
|---|---|---|---|
| YC7015 | Bacillus methylotrophicus (EU194897) | 99.68 | ++ |
| YC7016 | Bacillus methylotrophicus (EU194897) | 99.64 | ++ |
| YC7022 | Bacillus thuringiensis (ACNF010000156) | 99.87 | ++ |
| YC7023 | Bacillus cereus (AE016877) | 100 | ++ |
| YC7025 | Bacillus simplex (AB363738) | 98.88 | ++ |
| YC7027 | Bacillus daliensis (ACNF010000156) | 100 | ++ |

[a]Based on the partial analysis of 16S rRNA gene sequences.
[b]The mycelial growth of a pathogen by antagonistic bacteria was determined as inhibition zone on PDA. +: 2-10, ++: 10-15, +++: 15-20, and ++++: >20 mm.

TABLE 12

| Plant pathogens | Inhibition zone[a] (mm) |
|---|---|
| Fusarium fujikuroi KACC 44022 | 28.0 ± 0.6 |
| Magnaporthe grisea KACC 40415 | 29.0 ± 0.6 |
| Bipolaris oryzae KACC 40853 | 27.6 ± 0.3 |
| Rhizoctonia solani KCTC 40101 | 23.6 ± 0.3 |
| Sclerotinis sclerotiorum GSCC 50501 | 28.0 ± 0.6 |
| Botrytis cinerea KCTC 6973 | 27.3 ± 0.3 |
| Fusarium oxysporum KCTC 16909 | 25.0 ± 0.6 |
| Botryosphaeria dothidea GSCC 50201 | 24.6 ± 0.3 |
| Pythium ultimum GSCC 50651 | 28.3 ± 0.3 |
| Alternaria panax KACC 42461 | 10.0 ± 0.6 |

Figure 9A:
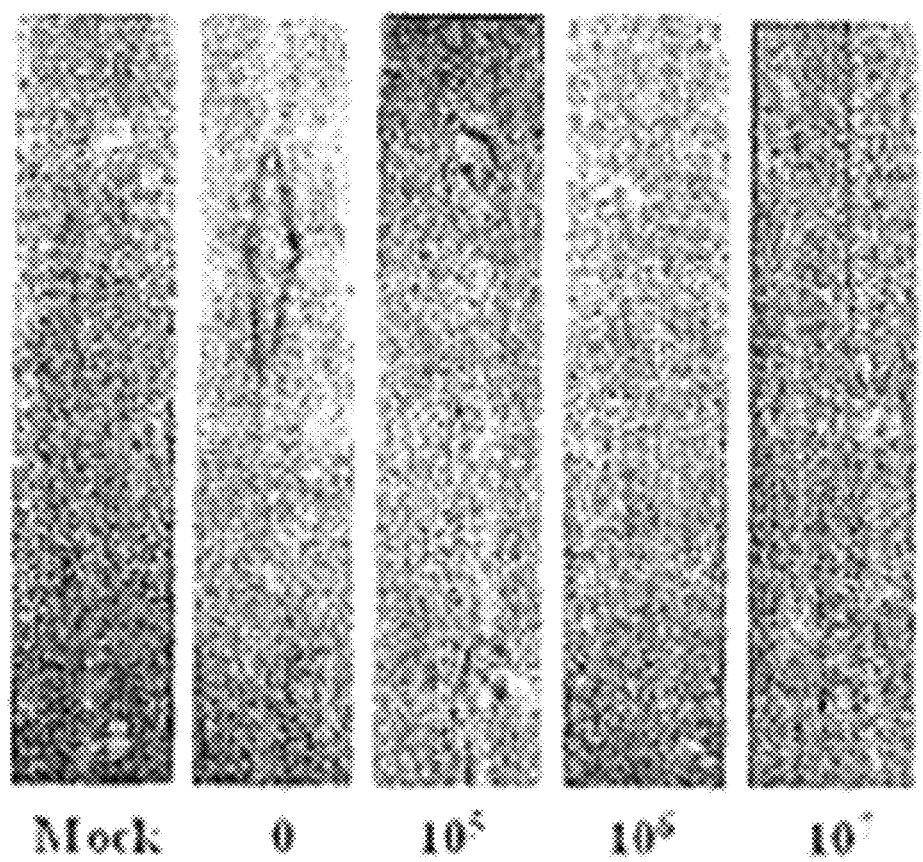
FIG. 9(*a*) is a photograph and FIG. 9(*b*) is a graph illustrating results of investigating activity for inducing systemic acquired resistance to rice bacterial blight and panicle blight relative to YC7007 strain.
Figure 9B:
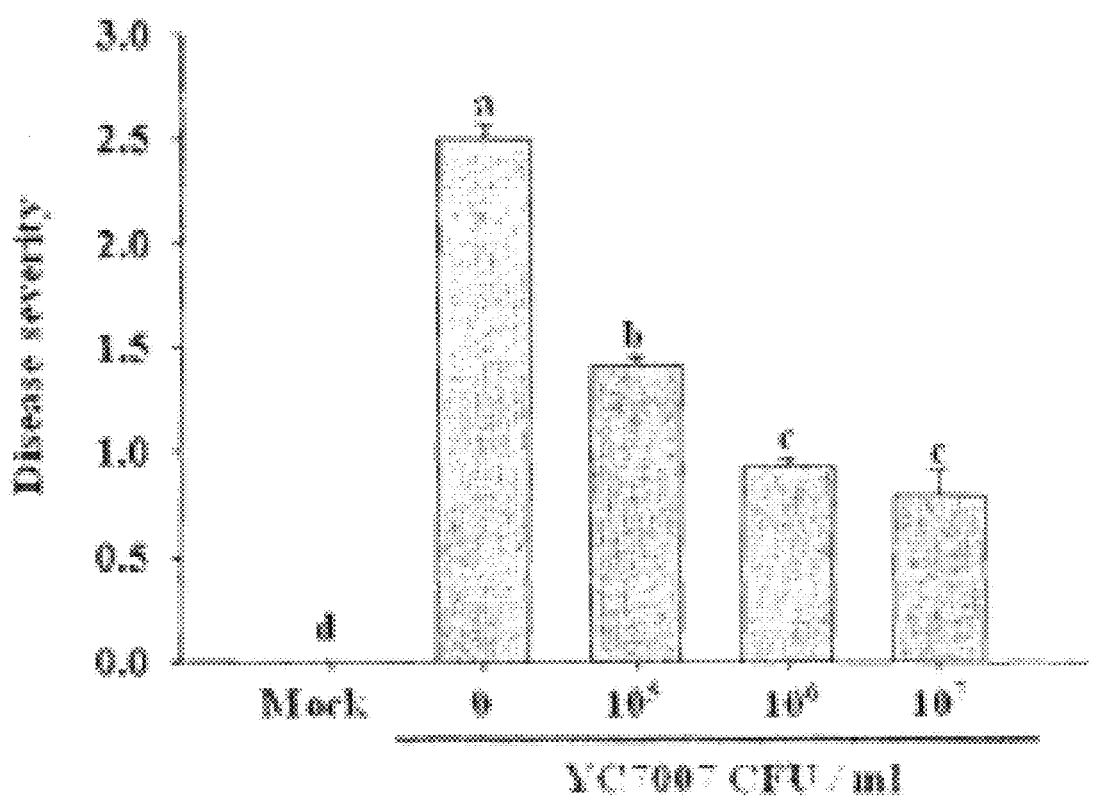

(2) Induction of Systemic Acquired Resistance to Panicle Blight and Bacterial Blight With regard to YC7007 strain, a systemic acquired resistance to the bacterial blight and panicle blight was investigated. As a result of drenching YC7007 strain at different concentrations ($5.6 \times 10^5$, $3.6 \times 10^6$ and $2 \times 10^7$ CFU/ml) into soil, it was found that, compared to the control group having a disease attack degree of leaf rot (2.5), the above strain could considerably reduce the disease attack degree to 1.4, 0.9 and 0.8, respectively, (p<0.05) (see FIGS. 9(a) and 9(b)). However, there was no significant difference in the concentration between $10^6$ and $10^7$. When drenching YC7007 strain at a concentration of $2 \times 10^7$ CFU/ml into rhizospheric soil, it could be seen that effects of preventing the panicle blight and bacterial blight were 65.2% and 61.2%, respectively, thereby being excellent. Further, in a case of foliar spraying the culture filtrate, it could be seen that disease attack degrees of the panicle blight and the bacterial blight were considerably reduced by about 70.8% and 70.5%, respectively, compared to the control group (see Table 13 below). Therefore, it could be seen that the YC7007 strain greatly reduced the disease attack degrees of the panicle blight and bacterial blight (p<0.01), compared to the control group.

TABLE 13

| | Disease severity Pathogen[y] | | % Disease reduction | |
|---|---|---|---|---|
| Treatment[x] | B. glumae | X. oryzae pv. oryzae | B. glumae | X. oryzae pv. oryzae |
| Control | 2.50 ± 0.08 a | 5.67 ± 0.13 a | — | — |
| YC7007 (suspension) | 0.87 ± 0.12 b | 2.20 ± 0.23 b | 65.2 | 61.2 |
| YC7007 (culture filtrate) | 0.73 ± 0.07 b | 1.67 ± 0.13 bc | 70.8 | 70.5 |

Different letters indicate values that are significantly different (P < 0.01) by Duncan's multiple range tests. Mean ± SE; standard error was calculated using 10 plants with there replicates for each treatment.

(3) Growth Promotion by YC7007

Compared to the control group, YC7007 strain showed to have frequently high growth promoting activity (p<0.05) in all experimental stages including seedling, tillering and booting stages of the rice. In the seedling stage, a length of sprouts in a test tube was increased from 11.67 cm to 19.33 cm by treatment of rice rhizosphere using a bacteria suspension ($2 \times 10^7$ CFU/ml). Similarly, the length of sprouts was increased from 36.45 cm to 46.33 cm in the tillering stage while increasing from 55.33 cm to 61.0 cm in the booting stage, respectively. Further, a length of the main root was increased from 2.67 cm to 7.67 cm in the seedling stage, while the number of tillers were increased from 1.9 to 2.9 and from 5.3 to 7.0, respectively, in the tillering stage and the booting stage (see Table 14 below).

TABLE 14

| | Growth promoting activity | | | | | |
|---|---|---|---|---|---|---|
| | Seedling stage[x] | | Tillering stage[y] | | Booting stage[z] | |
| Treatment | Shoot length (cm) | Root length (cm) | Shoot length (cm) | Tiller no. | Shoot length (cm) | Tiller no. |
| Control | 11.67 ± 0.33 b | 2.67 ± 0.33 b | 36.45 ± 1.18 b | 1.89 ± 0.22 b | 55.33 ± 0.33 b | 5.33 ± 0.67 b |
| YC7007 | 19.33 ± 0.33 a | 7.67 ± 0.33 a | 46.33 ± 2.0 a | 2.89 ± 0.11 a | 61.0 ± 2.00 a | 7.00 ± 0.58 a |

Different letters indicate statistically significant differences between treatments by Student's t-test.
Mean ± SE; standard error was calculated using 10 plants with three replicates for each treatment.

(4) Identification of YC7007 and YC7010 Antagonistic Bacteria

Two endophytic bacteria YC7007 and YC7010 having the strongest antagonistic activity among 15 antagonistic bacteria were subjected to identification through multiple phase approach. These two strains have 16S rRNA gene sequences continuously extending by 1,513 bp, respectively, wherein these are aligned in the same form except for two nucleotides (database accession numbers KP203893 (YC7007) and KP201498 (YC7010[T]) in GenBank/EMBL/DDBJ) (see FIGS. 1(a) and 1(b)). By analysis of 16S rRNA gene sequences, it was demonstrated that both of these strains are present in the same clade having the same branch length in the phylogenetic tree, and exhibited the highest similarity to *B. siamensis* KACC 15859$^T$ (99.67%), *B. methylotrophicus* KACC 13105$^T$ (99.65%), *B. amyloliquefaciens* subsp. *plantarum* KACC 17177$^T$ (99.60%) and *B. tequilensis* KACC 15944$^T$ (99.45%) (see Table 11 above and FIG. 2). A DNA-DNA relatedness value between the YC7010 strain and the most similar allied strain, that is, *B. siamensis* KACC 15859$^T$, was 50.4±3.5. However, the DNA-DNA relatedness value between YC7007 and YC7010 was 91.5±11.0% (see Table 2 above). The above two strains are gram-positive, have mobility with a bar form and show preferable growth at a temperature of 13 to 60° C. (optimum 28 to 30° C.) and pH 4 to 12 (optimum pH 7). These strains could be grown in 0.1 TSA medium containing 1 to 13% (w/v) sodium chloride, however, not necessarily requiring sodium chloride for the growth. The strains have resistance to chloramphenicol at a concentration of 30 μg/ml. Further, the strains included meso-diaminopimelic acid as antagonistic diamino acid in cell wall peptidoglycan, and MK-7 as a major respiratory quinone system. Other physiological and biochemical characteristics of YC7007 and YC7010 strains are shown in Table 1 above. It could be seen that major fatty acids of YC7007 and YC7010 strains, respectively, were anteiso-$C_{15:0}$ (38.4 and 32.0%) and iso $C_{15:0}$ (28.1 and 27.7%). Other cell fatty acid profiles of YC7010 were composed of $C_{16:0}$ (7.7%), iso $C_{17:0}$ (6.4%), anteiso-$C_{17:0}$ (5.3%), iso $C_{16:0}$ (5.2%), $C_{18:0}$ (5.1%), $C_{16:1}$ω7c alcohol (3.4%), iso $C_{14:0}$ (2.9%), iso-$C_{17:1}$ ω10c (1.7%), $C_{16:1}$ ω11c (1.4%), $C_{14:0}$ (1.1%) and $C_{20:1}$ ω7c (0.2%) (see Table 3 above). G+C content of genomic DNA in the YC7007 and YC7010 strains were 50.5 mol % and 51.2 mol %, respectively. The strains showed a specific polar lipid profile consisting of phosphatidylethanolamine (PE), phosphatidylglycerol (PG), diphosphatidylglycerol (DPG), unknown glycolipid (GL) and unknown aminolipids (AL1-2). As a result of 16S rRNA gene sequence analysis, the DNA-DNA relatedness value, composition of fatty acid, and biochemical and physiological characteristics, the YC7007 and YC7010 strains were identified as a novel species of *Bacillus* genus, thereby being suggested as *Bacillus oryzicola* sp. nov.

(5) Specification of *Bacillus oryzicola* YC7010$^T$ Sp. Nov.

The cell is gram-positive with a bar form (0.8-0.9×2.0-3.0 μm). A colony grown in a R2A agar medium at 28° C. for 2 days has a white-cream color and is in a circular and flat elevation form with an entire margin. The cell is a single polar flagellum having mobility. The cell wall is an antagonistic diamino acid and contains meso-diaminopimelic acid. In general, the cell is expressed to be catalase-positive and oxidase-negative alone or in a pair, and grown at 13 to 60° C. and pH 4 to 12.0. The cell is positive to casein and gelatine hydrolysis but negative to starch, Tween 20, Tween 80, tyrosin and carboxymethyl cellulose. Further, the cell spends D-glucose, D-fructose, D-mannose, D-mannitol, methyl-α-D-glucopyranoside, N-acetyl-glucosamine, amygdalin, arbutin, esculin ferric citrate, salicin, D-celiobiose, D-maltose, D-lactose, D-saccharose, D-trehalose, D-raffinose, starch, glycogen, gentiobiose, trisodium, citrate and Kohn's gelatine. Further, as a result of API ZYM kit, the cell shows enzymatical activity of esterase (C4), esterase lipase (C8), naphthol-AS-Bl-phosphohydrolase and N-acetyl-β-glucosaminidase, however, does not show activity to lipase (C-14), leucine arylamidase, valine arylamidase, cystine arylamidase, trypsin, α-chymotrypsin, α-galactosidase, β-galactosidase, β-glucosidase, α-mannosidase and α-fucosidase. Further, the cell has resistance to chloramphenicol and streptomycin at a concentration of 30 μg/ml, however, may accept ampicillin, penicillin and gentamycin at a concentration of 10 μg/ml and kanamycin, vancomycin and tetracycline at a concentration of 30 μg/ml. The growth of cell could be observed in R2A culture solution containing 13% (w/v) sodium chloride, however, not in the same culture solution containing 14% (w/v) sodium chloride. Major quinone is MK-7. The polar lipid may include phosphatidylethanolamine (PE), phosphatidylglycerol (PG), diphosphatidylglycerol (DPG), unknown glycolipid (GL) and unknown aminolipids (AL1-2). DNA G+C content of the type strain is 51.2 mol %. Type strain YC7010$^T$ (=KACC18228$^T$) was isolated from the rice roots (Jinju, Korea).

As described above, the present example demonstrated that, among diverse endophytic strains isolated from the rice roots, 6% of *Bacillus* genus was antagonistic and could inhibit the growth of hypha of plant pathogens. According to previous studies, it was reported that about 9% of *Bacillus* genus and other gram-negative bacteria-containing endophytic bacteria isolated from plants living in a mud flat are antagonistic to oomycetous phytopathogens (see Non-Patent Document 7). According to 16S rRNA gene sequences, some strains of the present invention belonging to *Bacillus* genus were demonstrated to have antagonistic activity to major rice fungal and bacterial pathogens in vitro and in vivo experiments. Among these isolated strains, the YC7007 and YC7010 stains having the highest similarity to *B. siamensis* exhibited strong antagonistic activity to inhibit the growth of hypha of *F. fujikuroi*, which is a bakanae pathogen and the most significant rice seed-derived pathogen. Further, a culture filtration of YC7007 also has strong inhibitory activity to bakanae, bacterial blight and grain rot of the rice, and therefore, may be recognized as a strain producing an anti-fungal material. Some in *Bacillus* genus may generate a small amount of peptide and lipopeptide such as fengycin, iturin and surfactin, and have been reported to express good inhibitory efficacy to the plant pathogens (Bais, H. P., Fall, R. and Vivanco, J. M. 2004. Biocontrol of *Bacillus subtilis* against infection of *Arabidopsis* roots by *Pseudomonas syringae* is facilitated by biofilm formation and surfactin production. *Plant Physiol.* 134:307-319; Crane, J. M., Gibson, D. M., Vaughan, R. H. and Bergstrom, G. C. 2013. Iturin levels on wheat spikes linked to biological control of *Fusarium* head blight by *Bacillus amyloliquefaciens*. *Phytopathology* 103:146-155; Dimkic, I., Zivkovic, S., Beric, T., Ivanovic, Z., Gavrilovic, V., Stankovic, S. and Fira, D. 2013. Characterization and evaluation of two *Bacillus* strains, SS-12.6 and SS-13.1, as potential agents for the control of phytopathogenic bacteria and fungi. *Biol. Control* 65:312-321.). It was found from a pot test that the attack of panicle blight and bacterial blight could be inhibited by drenching a cell suspension of YC7007 strain, and this result may mean the induction of a systemic resistance. The disease attack degree of panicle blight was reduced by treatment using YC 7007 strain at a concentration of $10^5$ (CFU/ml), and at a higher concentration of $10^6$ to $10^7$ CFU/ml, the disease attack was inhibited by 62% or more. Further, YC7007 culture filtrate reduced 70% or more of disease attack of the panicle blight and bacterial blight, compared to the control group. It was also discovered that treatment using a cell suspension of *B. subtilis* ($2.5 \times 10^8$ CFU/ml) and *B. cereus* AR156 ($5 \times 10^8$ CFU/ml) could control speck diseases of *Arabidopsis* roots and leaves, respectively (Bais et al., 2004; Niu, D. D., Liu, H. X., Jiang, C. H., Wang, Y. P., Wang, Q. Y., Jin, H. L. and Guo, J. H. 2011. The plant growth promoting rhizobacterium *Bacillus cereus* AR156 induces systemic resistance in *Arabidopsis thaliana* by simultaneously activating salicylate- and jasmonate/ethylene dependent signaling pathways. *Mol. Plant-Microbe Interact.* 24:533-542.). Since the bacteria concentration of *B. subtilis* and *B. cereus* AR156 is $10^8$ CFU/ml, which is 100 times higher than YC7007 ($10^6$ CFU/ml), it is not realistic in practically using these bacteria by agricultural farm houses. In order to develop antagonistic bacteria as biopesticides, the optimum concentration should be in a level of $10^7$ CFU/ml or less, when considering a dilution factor for final use by a user (Chen, X. H., Scholz, R., Borriss, M., Junge, H., Mogel, G., Kunz, S. and Borriss, R. 2009. Difficidin and bacilysin produced by plant associated *Bacillus amyloliquefaciens* are efficient in controlling fire blight disease. *J. Biotechnol.* 140:38-44.). By drenching the bacteria suspension having antagonistic activity to pathogens into rice rhizosphere and foliar spraying a culture filtrate, YC7007 strain may directly and/or indirectly interact between the pathogens. The panicle blight and bacterial blight could be prevented by such drenching or foliar spraying treatment, and it is presumed that such prevention may be achieved since YC7007 strain acts through induced systemic resistance (ISR) or systemic acquired resistance (SAR), thus to inhibit diseases (Ahn, I. P., Lee, S. W. and Suh, S. C. 2007. Rhizobacteria induced priming in *Arabidopsis* is dependent on ethylene, jasmonic acid, and NPR1. *Mol. Plant-Microbe Interact.* 20:759-768; Niu et al., 2011). A reaction mechanism needs to be determined in an aspect of hormone signals through salicyclic, jasmonic or ethylene pathway, in regard to SAR or ISR.

A variety of *Bacillus* species have a sustaining power for a long period of time even in unfavorable environments, thus to be commercialized as biopesticides. Some species may induce systemic acquired resistance, and therefore, actually function in diverse plants (Hu et al., 2011; Kloepper et al., 2004). *B. vallismortis* EXTN-1 and *B. cereus* have been used for prevention of rice blast, rice sheath blight and bakanae diseases (Kazempour and Elahinia, 2007; Park et al., 2006). It is believed such a finding that *Bacillus* strain YC7007 has long term sustained activity to major bacterial diseases such as panicle blight and bacterial blight was reported according to the present study for the first time. Moreover, it was demonstrated that YC7007 strain is effective to promote the growth of rice by applying the bacteria suspension once in the seedling stage immediately after germination. Compared to the control group, YC7007 strain has increased not only the length of sprouts and roots by 1.1 to 2.9 times in the seedling stage, tillering stage and booting stage, but also the number of tillers in the tillering stage and booting stage. These findings mean that activates for the induction of resistance and promotion of growth by probiotic bacterium YC7007 are continued for a long time from the seedling stage to the booting stage (Picard, C., Baruffa, E. and Bosco, M. 2008. Enrichment and diversity of plant probiotic microorganisms in the rhizosphere of hybrid maize during four growth cycles. *Soil Biol. Biochem.* 40:106-115.). It is known that the induction of host resistance may adversely affect the host plant, since it inhibits the growth associated with plant growth hormones such as gibberellin acid and oxine. An immune system is controlled by brassinosteroids and salicylic acid that at least partially inhibit gibberellin acid and oxine through interaction with hormones (negative cross-talk) in the rice and *Arabidopsis* (De Vleesschauwer, D., Van Buyten, E., Satoh, K., Balidion, J., Mauleon, R., Choi, I. R., Vera Cruz, C., Kikuchi, S. and Hofte, M. 2012. Brassinosteroids antagonize gibberellin and salicylate mediated root immunity in rice. *Plant Physiol.* 158:1833-1846; Wang, D, Mukhtar, K. P., Culler, A. H. and Dong, X. 2007. Salicylic acid inhibits pathogen growth in plants through repression of the auxin signaling pathway. *Curr. Biol.* 17:1784-1790.). Chemical derivatives of salicylic acid and benzothiadiazole (BTH) may induce systemic acquired resistance to biotrophic pathogens through a salicylic acid signal network in the rice, cucumber, *Arabidopsis*, and pepper, while inhibiting an oxine reaction to delay the growth of plant. On the other hand, some rhizospheric bacteria including *Bacillus* species may increase the induction of resistance without adverse effect to the growth of plant (Ahn et al., 2005; Ryu et al., 2004; Yang, J. W., Yu, S. H. and Ryu, C. M. 2009. Priming of defense-related genes confers root-colonizing Bacilli-elicited induced systemic resistance in pepper. *Plant Pathol. J.* 25:389-399.). In view of these aspects, it is considered that YC7007 strain may be a good candidate for development of biopesticides having multiple functions such as induction of resistance and growth promotion in the rice without any adverse effect. Further, it is thought that YC7007 strain has anti-fungal and anti-bacterial activities through production of antibiotic materials.

According to the present invention, two endophytic strains named YC7007 and YC7010 have been more characterized on the basis of multiple phase study including 16S rRNA gene sequence, DNA-DNA hybridization, fatty acid analysis and other physical and biochemical experiments. These strains were identified as a novel species of *Bacillus* genus in the same clade having the same branch length in a phylogenetic tree. These two strains have the same whole sequence branching rate as each other, however, were different from other allied species in the clade of the phylogenetic tree. YC7007 and YC7010 strains showed 100% similarity to each other and also quite a high DNA-DNA relatedness value of 91.5%, therefore, both of these strains have been proved as the same *Bacillus* species. Compared to YC7010 type strain, a DNA-DNA hybridization value of other allied strains such as *B. siamensis, B. methylotrophicus, B. subtilis* subsp. *inaquosorum, B. amyloliquefaciens* subsp. *plantarum* and *B. tequilensis*, or the like, is generally less than 70%. Therefore, it could be understood that YC7010 strain is a novel species (Goris, J., Konstantinidis, K. T., Klappenbach, J. A., Coenye, T., Vandamme, P. and Tiedje, J. M. 2007. DNA-DNA hybridization values and their relationship to whole genome sequence similarities. *Int. J. Syst. Evol. Microbiol.* 57:81-91; Stackebrandt, E. and Goebel, B. M. 1994. Taxonomic Note: A place for DNA-DNA reassociation and 16s rRNA sequence analysis in the present species definition in bacteriology. *Int. J. Syst. Bacteriol.* 44:846-849.). Further, these two strains showed almost similar responses in the physical and biochemical experiments using API kits, while having different responses to other referential type strains. Therefore, it could be understood that the above two strains are distinguishable from other allied *Bacillus* strains. Due to a tolerance to sodium chloride, two strains were survived until 13% sodium chloride. On the other hand, *B. methylotrophicus* was not survived even at 10% sodium chloride (see Non-Patent Document 1). Major fatty acids of YC7007 and YC7010 are anteiso-$C_{15:0}$ and iso $C_{15:0}$, which are same as those of other allied species of *Bacillus* genus. On the other hand, a minor amount of other fatty acids in these two strains was different from that of allied species *Bacillus* strains. Individual bacteria have different fatty acid profiles, and analysis of such fatty acid is effectively used in identification of bacteria (Kampfer, P. 1994. Limits and possibilities of total fatty acid analysis for classification and identification of *Bacillus* species. *Syst. Appl. Microbiol.* 17:86-98.). Like the type strain of *Bacillus* genus, major isoprenoid quinone of YC7007 and YC7010 strains was menaquinone-7 (MK-7)

(Chen, J. H., Tian, X. R., Ruan, Y., He, Z. Q., Tang, S. K., Li, W. J., Shi, H. and Chen, Y. G. 2015. *Bacillus crassostreae* sp., nov., isolated from an oyster in the South China Sea. *Int. J. Syst. Evol. Microbiol.* Doi:10.1099/ijs. 0.000139; Kang, H., Weerawongwiwat, V., Kim, J. H., Sukhoom, A. and Kim, W. 2013. *Bacillus songkensis* sp. nov., isolated from soil. *Int. J. Syst. Evol. Microbiol.* 6/3:4189-4195.). DNA G+C contents of two strains are similar to each other and range from 50.5 to 51.2 mol %, which is however a little higher than other *Bacillus* species (see Non-Patent Document 1 and Non-Patent Document 17). Major polar lipids of two strains are PE, PG, and DPG which correspond to those of *B. siamensis* and *B. songklensis* (Kang et al., 2013; Non-Patent Document 17).

Based on all data of the multiple phase study, two strains YC7007 and YC7010 belonged to *Bacillus* genus, and therefore, these strains YC7007 and YC7010 were proposed as a novel species and named *Bacillus oryzicola* YC7010$^T$ sp. nov. as a type strain. Consequently, the endophytic strain *B. oryzicola* YC7007 is a strain having multi-functional activity, exhibits direct inhibition of fungal and bacterial pathogens, induction of systemic acquired resistance and plant growth promoting efficacies, thereby being practically applicable as a microorganism inoculant agent in the agricultural farm houses.

Exemplary embodiments of the present invention described above have been proposed to solve the conventional technical problems, and those skilled in the art will obviously understand that various alterations, modifications and additions are possible within the scope and spirit of the present invention. Such alterations and modifications are duly included in the appended claims.

The invention claimed is:

1. A novel microorganism *Bacillus oryzicola* YC7007 deposited with Korean Culture Center of Microorganisms (KCCM) having the address of KCCM, 361-221, Yurim B/D, Hongje-1-dong, Seodaemun-gu, Seoul 120-091, Republic of Korea under the Accession number of KCCM11275P on Apr. 18, 2012.

2. The *Bacillus oryzicola* according to claim 1, wherein the *Bacillus oryzicola* includes 16S rRNA having a base sequence represented by SEQ ID NO: 1.

3. The *Bacillus oryzicola* according to claim 1, wherein the *Bacillus* oryzicola has plant disease resistance inducing efficacy.

4. The *Bacillus oryzicola* according to claim 3, wherein the plant disease is at least one selected from a group consisting of grain rot, bacterial blight, panicle blight and bakanae disease.

5. The *Bacillus oryzicola* according to claim 3, wherein the *Bacillus oryzicola* further has plant pathogen inhibitory efficacy and plant growth promoting efficacy.

6. The *Bacillus* oryzicola according to claim 5, wherein the plant growth promoting efficacy is plant growth promoting efficacy in relation to rice.

7. A microorganism formulation for fertilizer, plant protection and plant enhancement use, comprising the microorganism according to claim 1, and a culture solution or culture filtrate thereof as an active ingredient.

* * * * *